(12) United States Patent
Parolini

(10) Patent No.: US 8,524,283 B2
(45) Date of Patent: Sep. 3, 2013

(54) T CELL IMMUNOMODULATION BY PLACENTA CELL PREPARATIONS

(75) Inventor: Ornella Parolini, Brescia (IT)

(73) Assignee: Centro di Ricerca E. Menni Fondazione Poliambulanza Istituto Ospedaliero, Brescia (IT)

( * ) Notice: Subject to any disclaimer, the term of this patent is extended or adjusted under 35 U.S.C. 154(b) by 445 days.

(21) Appl. No.: 12/664,713

(22) PCT Filed: Jun. 16, 2008

(86) PCT No.: PCT/EP2008/004845
§ 371 (c)(1),
(2), (4) Date: May 18, 2010

(87) PCT Pub. No.: WO2008/151846
PCT Pub. Date: Dec. 18, 2008

(65) Prior Publication Data
US 2010/0221268 A1    Sep. 2, 2010

(30) Foreign Application Priority Data
Jun. 15, 2007  (EP) .................................... 07011824

(51) Int. Cl.
*A61K 35/28*     (2006.01)
*A61K 35/26*     (2006.01)

(52) U.S. Cl.
USPC ........................................................ 424/577

(58) Field of Classification Search
None
See application file for complete search history.

(56) References Cited

U.S. PATENT DOCUMENTS

| | | | |
|---|---|---|---|
| 2,500,083 | A | 3/1950 | MacConnell |
| 5,649,989 | A | 7/1997 | Jones |
| 6,457,331 | B1 | 10/2002 | Kammonen |
| 2004/0231363 | A1 | 11/2004 | Monden et al. |
| 2006/0223177 | A1 | 10/2006 | Harris et al. |
| 2008/0248005 | A1* | 10/2008 | Phan .............................. 424/93.7 |
| 2010/0157712 | A1* | 6/2010 | Kim ............................... 365/222 |

FOREIGN PATENT DOCUMENTS

| | | |
|---|---|---|
| EP | 0705796 | 4/1996 |
| EP | 1288293 A1 | 3/2003 |
| WO | WO2006071794 A2 | 7/2006 |
| WO | WO 2008/146992 * | 4/2008 |

OTHER PUBLICATIONS

Feldman et al (Transplant. Proc. 1998, 30, 4126-4127.*
Cochlovius et al., Modern Drug Discovery, 2003, pp. 33-38.*
Laurence et al ( Nature Immunol, 2007, v.9, pp. 903-905.*
Mestas et al ( J. of Immunology, 2004, 172, pp. 2731-238.*
Pan et al . I of Clinical Neuroscience, 2007, pp. 1089-1098).*
Bailo et al., "Engraftment Potential of Human Amnion and Chorion Cells Derived from Term Placenta", article in Transplantation journal, Nov. 27, 2004, vol. 78, No. 10, pp. 1439-1448, Lippincott Williams & Wilkins.

Zhao et al., "Human Amniotic Mesenchymal Cells Have Some Characteristics of Cardiomyocytes", article in Transplantation journal, Mar. 15, 2005, vol. 79, No. 5, pp. 528-535, Lippincott Williams & Wilkins.
Portmann-Lanz et al., "Placental mesenchymal stem cells as potential autologous graft for pre- and perinatal neuroregeneration", article in American Journal of Obstetrics and Gynecology, 2006, pp. 664-673.
Alviano et al., "Term amniotic membrane is a high throughput source for multipotent mesenchymal stem cells with the ability to differentiate into endothelial cells in vitro", online article in BMC Development Biology journal found at http://www.biomedcentral.com/1471-213X/7/11, Feb. 21, 2007.
Dominici et al., "Minimal criteria for defining multipotent mesenchymal stromal cells. The International Society for Cellular Therapy position statement", position paper in Cytotherapy journal, 2006, vol. 8, No. 4, pp. 315-317, Taylor & Francis Group.
Le Blanc, "Mesenchymal stromal cells: tissue repair and immune modulation", article in Cytotherapy journal, 2006, vol. 8, No. 6, pp. 559-561, Taylor & Francis Group.
Rasmusson, "Immune modulation by mesenchymal stem cells", online review article in Experimental Cell Research 312 (2006) journal found at http://www.elsevier.com/locate/yexcr, pp. 2169-2179, Elsevier Inc.
Friedenstein et al., "Heterotopic Transplants of Bone Marror", article in Transplantation journal, Mar. 1968, vol. 6, No. 2, pp. 230-247, The Williams & Wilkins Co.
Jul. 21, 2010, Office Action in EP08773473, which share the same priority as this U.S. application.
Kern et al., "Comparative Analysis of Mesenchymal Stem Cells from Bone Marrow, Umbilical Cord Blood, or Adipose Tissue", article in Stem Cells 24 journal, 2006, pp. 1294-1302.
Lee et al., "Isolation of multipotent mesenchymal stem cells from umbilical cord blood", article in Blood journal, Mar. 1, 2004, vol. 103, No. 5, pp. 1669-1675, The American Society of Hematology.
Romanov et al., "Searching for Alternative Sources of Postnatal Human Mesenchymal Stem Cells: Candidate MSC-Like Cells from Umbilical Cord", article in Stem Cells 21 journal, 2003, pp. 105-110.
Lee et al., "Mesenchymal stem cells from cryopreserved human umbilical cord blood", online article in Biochemical and Biophysical Research Communications 320 (2004) journal found at http://www.elsevier.com/locate/ybbrc, pp. 273-278, Elsevier Inc.

(Continued)

*Primary Examiner* — Michail Belyavskyi
(74) *Attorney, Agent, or Firm* — Kolisch Hartwell, P.C.

(57) ABSTRACT

A Method for obtaining amniotic mesenchymal tissue cells (AMTC) and/or chorionic mesenchymal tissue cells (CMTC) comprises a) isolating amniotic membrane and/or chorionic membrane from human placenta and/or separating amniotic and chorionic membrane, a) washing the membrane of step a) to remove contaminants b) cutting the membrane of step b) c) incubating the membrane fragments of step c) in a medium containing dispase for 5 to 15 minutes at 33 to 42° C. d) incubating the composition of step d) in a resting solution for 5 to 15 minute at room temperature e) repeating steps d) and e) 0 to 6 times f) if chorionic membrane is involved peeling the stromal layer from the trophoblastic layer of the chorionic membrane of step e or f) g) digesting the fragments obtained in step e), f), or g) respectively, with collagenase for 1 to 5 hours at 33 to 42° C. h) collecting AMTCs and/or CMTCs from the suspension obtained in step h).

15 Claims, 11 Drawing Sheets

(56) References Cited

OTHER PUBLICATIONS

Villaron et al., "Mesenchymal stem cells are present in peripheral blood and can engraft after allogeneic hematopoietic stem cell transplantation", article in haematologica the hematology journal, Dec. 2004, pp. 1421-1427.

Roufosse et al., "Circulating mesenchymal stem cells", review article in The International Journal of Biochemistry & Cell Biology 36 (2004) journal found at http://www.elsevier.com/locate/ijbcb, pp. 585-597, Elsevier Inc.

De Coppi et al., "Isolation of amniotic stem cell lines with potential for therapy", article in Nature Biotechnology Advanced Online Publication, Jan. 7, 2007, pp. 1-7.

Di Nicola et al., "Human bone marrow stromal cells suppress T-lymphocyte proliferation induced by cellular or nonspecific mitogenic stimuli", article in Blood journal, May 15, 2002, vol. 99, No. 10, pp. 3838-3843, The American Society of Hematology.

Krampera et al., "Bone marrow mesenchymal stem cells inhibit the response of naive and memory antigen-specific T cells to their cognate peptide", article in Blood journal, May 1, 2003, vol. 101, No. 9, pp. 3722-3729, The American Society of Hematology.

Le Blanc et al., "Mesenchymal Stem cells Inhibit and Stimulate Mixed Lymphocyte Cultures and Mitogenic Responses Independently of the Major Histocompatibility Complex", article in Scandinavian Journal of Immunology 57, 2003, pp. 11-20, Blackwell Publishing Ltd.

Ueta et al., "Immunosuppressive properties of human amniotic membrane for mixed lymphocyte reaction", article in Clin Exp Immunol 2002, pp. 464-470, Blackwell Science.

Barry et al., "Immunogenicity of Adult Mesenchymal Stem Cells: Lessons from the Fetal Allograft", article in Stem Cells and Development 14, 2005, pp. 252-265.

Maccario et al., "Interaction of human mesenchymal stem cells with cells involved in alloantigen-specific immune response favors the differentiation of CD4+ T-cell subsets expressing a regulatory/suppressive phenotype", research paper in haematologica the hematology journal, 2005, pp. 516-525.

Beyth et al., "Human mesenchymal stem cells alter antigen-presenting cell maturation and induce T-cell unresponsiveness", article in Blood journal, Mar. 1, 2005, vol. 105, No. 5, pp. 2214-2219, The American Society of Hematology.

Aggarwal et al., "Human mesenchymal stem cells modulate allogeneic immune cell responses", article in Blood journal, Feb. 15, 2005, vol. 105, No. 4, pp. 1815-1822, The American Society of Hematology.

Zhang et al., "Human placenta-derived mesenchymal progenitor cells support culture expansion of long-term culture-initiating cells from cord blood CD34+ cells", article in Experimental Hematology 32 (2004) journal, pp. 657-664, Elsevier Inc.

Jiang et al., "Human mesenchymal stem cells inhibit differentiation and function of monocyte-derived dendritic cells", article in Blood journal, May 15, 2005, vol. 105, No. 10, pp. 4120-4126, The American Society of Hematology.

Nauta et al., "Mesenchymal Stem Cells Inhibit Generation and Function of Both CD34+-Derived and Monocyte-Derived Dendritic Cells", article in The Journal of Immunology, 2006, pp. 2080-2087.

Zappia et al., "Mesenchymal stem cells ameliorate experimental autoimmune encephalomyelitis inducing T-cell anergy", article in Blood journal, Sep. 1, 2005, vol. 106, No. 5, pp. 1755-1761, The American Society of Hematology.

Le Blanc et al., "Treatment of severe acute graft-versus-host disease with third party haploidentical mesenchymal stem cells", article in The Lancet journal, May 1, 2004, vol. 363, pp. 1439-1441, The Lancet Publishing Group.

Wolbank et al., "Dose-Dependent Immunomodulatory Effect of Human Stem Cells from Amniotic Membrane: A Comparison with Human Mesenchymal Stem Cells from Adipose Tissue", article in Tissue Engineering journal, Nov. 6, 2007, vol. 113, No. 6, pp. 1-11.

Billingham et al., "'Actively Acquired Tolerance' of Foreign Cells", article in Nature journal, Oct. 3, 1953, vol. 172, No. 4379, pp. 603-606, Nature Publishing Group.

Magati et al., "Human Amnion Mesenchyme Harbors Cells with Allogeneic T-Cell Suppression and Stimulation Capabilities", article in Stem Cells journal, 2008, pp. 182-192.

Collins, "Alcohol in Pregnancy", article in the Medical Journal of Australia, Aug. 23, 1980, pp. 173-175, Australasian Medical Publishing Co. Ltd.

Bonney et al., "The Maternal Immune System's Interaction with Circulating Fetal Cells", article in The Journal of Immunology, 1997, pp. 40-47.

Bonney et al., "Much IDO about pregnancy", article in Nature Medicine journal, Oct. 1998, vol. 4, No. 10, pp. 1128-1129.

Bianchi et al., "Biological implications of bi-directional fetomaternal cell traffic: a summary of a National Institute of Child Health and Human Development-sponsored conference", meeting report in The Journal of Maternal-Fetal and Neonatal Medicine, 2003, pp. 123-129.

Koch et al., "Natural mechanisms for evading graft rejection: the fetus as an allograft", article in Springer Semin Immunopathod, 2003, pp. 95-117.

Enders et al., "The Cytology of Hofbauer Cells", article in the Anatomical Record journal, pp. 231-236.

Sutton et al., "HLA-DR positive cells in the human placenta", article in Immunology journal, 1983, pp. 103-112.

Sutton et al., "Cells bearing Class II MHC antigens in the human placenta and amniochorion", article in Immunology journal, 1986, pp. 23-29.

Bulmer et al., "Expression of class II MHC gene products by macrophages in human uteroplacental tissue", article in Immunology journal, 1988, pp. 707-714.

Fukuchi et al., "Human Placenta-Derived Cells Have Mesenchymal Stem/Progenitor Cell Potential", article in Stem Cells journal, 2004, pp. 649-658.

Chang et al., "Placenta-Derived Multipotent Cells Exhibit Immunosuppressive Properties That Are Enhanced in the Presence of Interferon-$\gamma$", article in Stem Cells journal, 2006, pp. 2466-2477.

Djouad et al., "Immunosuppressive effect of mesenchymal stem cells favors tumor growth in allogeneic animals", article in Blood journal, Nov. 15, 2003, vol. 102, No. 10, pp. 3837-3844, The American Society of Hematology.

Tse et al., "Suppression of Allogenic T-Cell Proliferation by Human Marrow Stromal Cells: Implications in Transplantations", article in Transplantation journal, Feb. 15, 2003, vol. 75, No. 3, pp. 389-397, Lippincott Williams & Wilkins.

Meisel et al., "Human bone marrow stromal cells inhibit allogenic T-cell responses by indoleamine 2, 3-dioxygenase-mediated tryptophan degradation", brief report in Blood journal, Jun. 15, 2004, vol. 103, No. 12, pp. 4619-4621.

Potian et al., "Veto-Like Activity of Mesenchymal Stem Cells: Functional Discrimination Between Cellular Responses to Alloantigens and Recall Antigens", article in the Journal of Immunology, 2003, pp. 3426-3434.

Klyushnenkova et al., "T cell responses to allogeneic human mesenchymal stem cells: immunogenicity, tolerance, and suppression", article in Journal of Biomedical Science, 2005, pp. 47-57.

Soncini et al., "Isolation and characterization of mesenchymal cells from human fetal membranes", article in Journal of Tissue Engineering and Regenerative Medicine, 2007, pp. 295-305.

Ortiz et al., "Upregulation of the p75 But Not the p55 TNF-$\alpha$ Receptor mRNA after Silica and Bleomycin Exposure and Protection from Lung Injury in Double Receptor Knockout Mice", article in American Journal of Respiratory Cell and Molecular Biology, 1977, vol. 20, pp. 825-833.

Mar. 26, 2008, Partial European Search Report from EP2014767A1 from European Patent Office, which is the publication of EP07011824, the priority application to this U.S. application.

May 18, 2009, Search Report from European Patent Office, in PCT/EP2008/004845, which is the international application for this U.S. application.

Ortiz et al., "Mesenchymal stem cell engraftment in lung is enhanced in response to bleomycin exposure and ameliorates its fibrotic effects", article in PNAS journal, Jul. 8, 2003, vol. 100, No. 14, pp. 8407-8411.

Ortiz et al., "Interleukin 1 receptor antagonist mediates the antiinflammatory and antifibrotic effect of mesenchymal stem cells during lung injury", article in PNAS journal, Jun. 26, 2007, vol. 104, No. 26, pp. 11002-11007.

Serrano-Mollar et al., "Intratracheal Transplantation of Alveolar Type II Cells Reverses Bleomycin-induced Lung Fibrosis", article in American Journal of Respiratory and Critical Care Medicine, 2007, vol. 176, pp. 1261-1268.

Parolini et al., "Human Placenta: a Source of Progenitor/Stem Cells?", article in Journal of Reproductive Medicine and Endocrinology, Feb. 2006, pp. 117-126.

Kobayashi et al., "Suppression of Corneal Neovascularization by Culture Supernatant of Human Amniotic Cells", article in Cornea journal, Jan. 2002, vol. 21, No. 1, pp. 62-67.

Anker et al., "Isolation of Mesenchymal Stem Cells of Fetal or Maternal Origin from Human Placenta", article Stem Cells journal, 2004, vol. 22, No. 7, pp. 1338-1345, Alphamed Press, Dayton, Ohio US.

Yan et al., "Nuclear factor kappa B activation and regulation of cyclooxygenase type-2 expression in human amnion mesenchymal cells by interleukin-1beta", article in Biology of Reproduction journal, Jun. 2002, vol. 66, No. 6, pp. 1667-1671.

Prockop, "Stem Cell Research Has Only Just Begun", Science Magazine Jul. 13, 2001, vol. 293, No. 5528, pp. 211-212.

Billington, "The immunological problem of pregnancy: 50 years with the hope of progress. A tribute to Peter Medawar", Journal of Reproductive Immunology 2003, pp. 1-11.

Parolini et al., "Concise Review: Isolation and Characterization of Cells from Human Term Placenta: Outcome of the First International Workshop on Placenta Derived Stem Cells", article in Stem Cells, Feb. 2008, vol. 26, No. 2, pp. 300-311, Dayton, Ohio US.

Kadner et al., "Human umbilical cord cells for cardiovascular tissue engineering: a comparative study", article in European Journal of Cardio-Thoracic Surgery, Apr. 2004, vol. 25, No. 4, pp. 635-641, Springer Verlag, Berlin, DE.

Parolini et al., "Isolation and Characterization from Human Term Placenta: Outcome of the First International Workshop on Placenta Derived Stem Cells", article in Stem Cells Express, published online at www.stemcells.com, Nov. 8, 2007.

Evangelista et al., "Placenta-derived stem cells: new hope for cell therapy?", article in Cytotechnology journal, Sep. 28, 2008, vol. 58, No. 1, pp. 33-42, Springer Science+Business Media BV.

Zhang et al., "Mesenchymal progenitor cells derived from chorionic villi of human placenta for cartilage tissue engineering", article in Biochemical and Biophysical Research Communications, Feb. 17, 2006, vol. 340, No. 3, pp. 944-952, Academic Press Inc., Orlando, Florida US.

Whittle et al., "The Characterization of Human Amnion Epithelial and Mesenchymal Cells: the Cellular Expression, Activity and Glucocorticoid Regulation of Prostaglandin Output", article in Placenta, May 2000, vol. 21, No. 4, pp. 394-401.

Zuk et al., "Multilineage Cells from Human Adipose Tissue: Implications for Cell-Based Therapies", Tissue Eng. 2001, vol. 7, No. 2, pp. 211-228.

Medawar, "Some Immunological and Endocrinological Problems Raised by the Evolution of Viviparity in Vertebrates.", Symp Soc Exp Biol 1953, vol. 7, pp. 320-338.

Moore et al, "Animal Models of Human Lung Disease. Murine models of pulmonary fibrosis", Am J Physiol Lung Cell Mol Physiol, Nov. 9, 2007, vol. 294, pp. L152-L160.

Chua et al., "Pulmonary Fibrosis. Searching for Model Answers", Respir Cell Mol Biol, 2005, vol. 33, pp. 9-13.

Izbicki et al., "Time course of bleomycin-induced lung fibrosis", International Journal of Experimental Pathology, 2002, vol. 83, pp. 111-119.

Moeller et al., "The bleomycin animal model: a useful tool to investigate treatment options for idiopathic pulmonary fibrosis", Int J Biochem Cell Biol. 2008, vol. 40, pp. 362-382.

Luzina et al., "Roles of T lymphocytes in pulmonary fibrosis", Journal of Leukocyte Biology, Feb. 2008, vol. 83, pp. 237-244.

* cited by examiner

● AMTC
■ AMTC HLADR-
▲ AMTC HLADR+

After 3 days from transplantation

After 14 days from transplantation

T CELL IMMUNOMODULATION BY PLACENTA CELL PREPARATIONS

CROSS-REFERENCE TO RELATED APPLICATION

This application is a national phase application of PCT/EP2008/004845, filed Jun. 16, 2008, which claims priority to European Patent Application No. 07011824.5, filed Jun. 15, 2007, each of which is hereby incorporated by reference.

BACKGROUND AND SUMMARY

The present invention is concerned with a method for obtaining amniotic mesenchymal tissue cells (AMTC) and/or chorionic mesenchymal tissue cells (CMTC) as well as UCC, with cells obtainable by these methods and the use of the cells and preparations.

Cells derived from the amniotic membrane of human placenta have been receiving particular attention because of their stem cell potentiality and immunomodulatory properties, which make them an attractive candidate source for cell therapy approaches.

In this study, we have isolated cells from the mesenchymal layer of amnion (AMTC) and studied their suppressant and stimulator characteristics. We found that unfractionated AMTC can inhibit T cell allogeneic proliferation responses even in the absence of direct cell contact, which points to the existence of suppressor soluble factor(s). In addition, we have identified two populations of AMTC discordant for expression of the HLA-DR, CD45, CD14, and CD86 cellular markers. While unfractionated, HLA-DR$^+$ and HLA-DR$^-$ AMTC populations fail to induce proliferation of resting allogeneic T cells. HLA-DR$^+$ AMTC induced strong proliferation of anti-CD3 primed allogeneic T cells in cell-cell contact settings. The revelation that cell populations from human amnion mesenchyme possess both suppressive and stimulatory properties sheds additional light on the immunomodulatory functions of this tissue and its critical role in fetal-maternal tolerance and supports the quest for cells with similar characteristics among mesenchymal cells from other tissues, including mesenchymal stromal cells (MSC).

The amnion and chorion mesenchymal layers from human term placenta harbor cells that present with fibroblast-like morphology, have clonogenic potential, display multi-potent differentiation capacity including osteogenic, adipogenic, chondrogenic, vascular, endothelial, cardiomyocyte, skeletal muscle lineages. [Bailo, 2004 #31; Zhao, 2005 #97; Portmann-Lanz, 2006 #96; Parolini, 2006 #64; Alviano, 2007 #93]. These characteristics are reminiscent of the properties described for bone marrow derived mesenchymal stromal cells (BM-MSC), a much more extensively characterized cell type which is gaining increasing interest for clinical applications [Dominici, 2006 #109; Le Blanc, 2006 #50; Rasmusson, 2006 #91].

Beside bone marrow, where they have been first described [Friedenstein, 1968 #51], other sources for MSC have been reported such as adipose tissue [Zuk, 2001 #65; Kern, 2006 #69; Lee, 2004 #107], cord blood [Romanov, 2003 #66; Lee, 2004 #68] peripheral blood [Villaron, 2004 #67; Roufosse, 2004 #74], amniotic fluid [De Coppi, 2007 #87].

One critical characteristic of MSC is their ability to suppress T cell proliferation in MLR [Di Nicola, 2002 #11; Krampera, 2003 #12; Le Blanc, 2003 #22; Ueta, 2002 #17; Barry, 2005 #88] in addition to other immunomodulatory properties, such as their induction of Th2 responses, up regulation of T regulatory cells [Maccario, 2005 #18; Beyth, 2005 #38; Aggarwal, 2005 #43] and inhibitory effects on maturation of dendritic cells [Zhang, 2004 #44; Aggarwal, 2005 #43; Maccario, 2005 #18; Jiang, 2005 #45; Nauta, 2006 #42].

Whether or not MSC can induce tolerance in allogeneic transplantation setting is still an area of debate [Zappia, 2005 #108; Barry, 2005 #88; Nauta, 2006 #42], however, decreased GvHD in allogenic stem cell transplantation and treatment of acute GvHD in vivo have been demonstrated [Le Blanc, 2004 #1; Le Blanc, 2006 #50].

We and others have shown that cells isolated from the mesenchymal region of human amnion and chorion fail to induce allogenic T cell responses and actively suppress T cell proliferation induced by alloantigens [Bailo, 2004 #31; Wolbank, 2007 #86]. Furthermore, we have shown that a heterogeneous population isolated from the human amnion and chorion fetal membranes demonstrated long term chimerism in xenogenic animal transplantation models, suggesting their reduced immunogenicity and tolerogenic potential [Bailo, 2004 #31].

It is tempting to speculate that the immunomodulatory characteristics of the mesenchymal cells resident within the fetal membranes play a role in the fetal-maternal tolerance process, however this theory remains to be proven.

Scientists have long been puzzled by the mechanisms involved in maternal tolerance to the fetus. Proposed explanations are the anatomical barrier between the mother and the fetus formed by the placenta, the immunologic inertness of the mother and the antigenic immaturity of the fetus [Medawar, 1953 #103]. However, several studies have indicated that the fetal placental barrier may be less inert or impervious than previously envisioned and presented evidence for cellular trafficking in both directions across the fetal/maternal interface [Collins, 1980 #102, Bonney, 1997 #80, Bianchi, 2003 #99]. In addition, it is now clear that the maternal immune system is not anergic to all fetal tissues since it can respond and eliminate fetal cells that enter the maternal circulation [Bonney, 1997 #80; Bonney, 1998 #82]. Finally, it is well accepted that fetal trophoblast cells lack the major histocompatibility complex (MHC) class II (MHC-II) antigens, downregulate MHC class I proteins, and express high levels of HLA-G, an antigen known to protect against rejection [Koch, 2003 #105]. However, fundamental questions that still remain are whether the fetus participates actively in suppressing maternal allogeneic immune responses and, if so, what fetal placental tissues play an immunomodulatory role. The mesodermal (stromal) layers of amnion and chorion are considered avascular and therefore inert in terms of immune presentation, however, macrophage-like populations in the chorion (Hofbauer cells) have been described in previous reports [Enders, 1970 #113]. More recently a defined population of HLA-DR-expressing cells with macrophage-monocyte phenotypic characteristics has also been described in the mesenchymal layer of the amnion [Sutton, 1986 #83; Sutton, 1983 #84; Bulmer, 1988 #85] thus suggesting the presence of populations capable of active immune function within these tissues.

In this study we set out extend our investigations on the immunomodulatory characteristics of amniotic cells and discovered that subfractions of cells isolated from the amniotic mesenchymal tissue can indeed induce either inhibitory or stimulating effects on allogeneic T lymphocytes.

It was the object of the present invention to provide a method for isolating and culturing cells that have an effect on the immune system. Moreover, it was the object of the present invention to provide medicaments that can be used to modulate, stimulate, suppress or otherwise influence the immune response. Moreover, it was the object to provide a medicament to avoid transplant rejection.

These objects are solved by the methods disclosed and the cells obtainable therewith as well as the medicaments and their use.

The inventors found that useful cells can be isolated from the amnion, chorion and umbilical cord.

DETAILED DESCRIPTION

Figure 1:
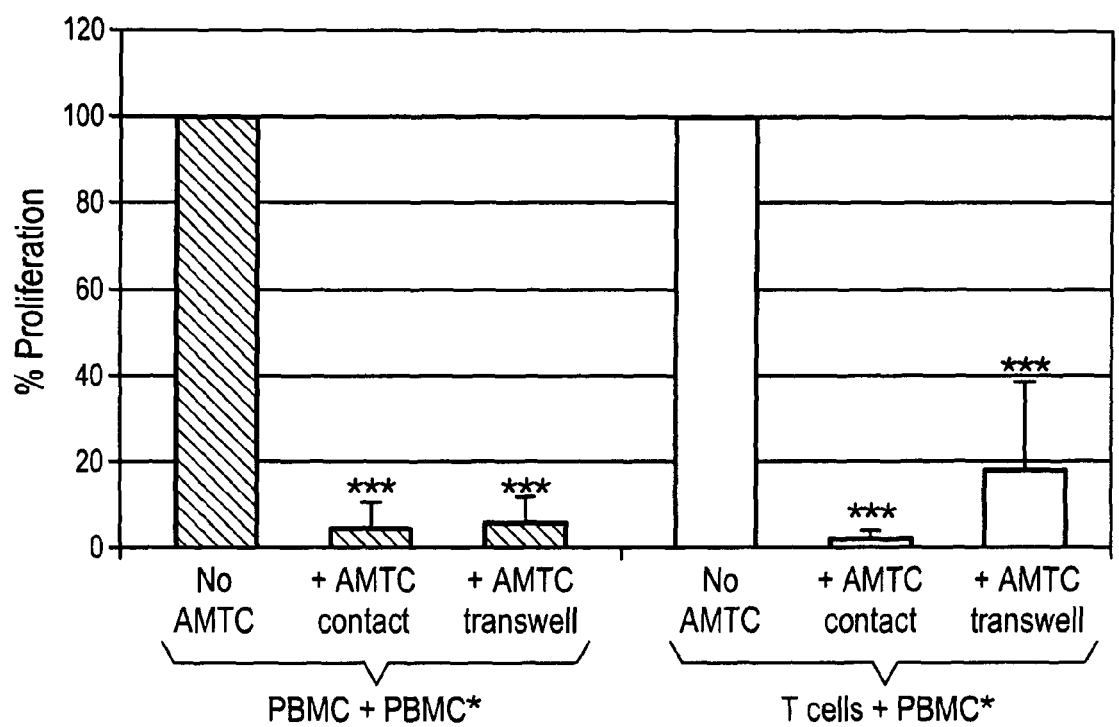
FIG. 1 is a graph showing suppression of allogeneic response by AMTC.

In accordance with the present invention a useful method for obtaining amniotic mesenchymal tissue cells (AMTC) and/or chorionic mesenchymal tissue cells (CMTC) comprises the following steps:

a) isolating amniotic membrane and/or chorionic membrane from human placenta and/or separating amniotic and chorionic membrane,
b) washing the membrane of step a) to remove contaminants
c) cutting the membrane of step b)
d) incubating the membrane fragments of step c) in a medium containing dispase for 5 to 15 minutes at 33 to 42° C.
e) incubating the composition of step d) in a resting solution for 5 to 15 minute at room temperature
f) repeating steps d) and e) 0 to 6 times
g) if chorionic membrane is involved peeling the stromal layer from the trophoblastic layer of the chorionic membrane of step e or f)
h) digesting the fragments obtained in step e), f), or g) respectively, with collagenase for 1 to 5 hours at 33 to 42° C.
i) collecting AMTCs and/or CMTCs from the suspension obtained in step h).

Particulars of this method are outlined in detail below. The media used for culturing, resting etc. are those normally used in this field, like PBS, RPMI 1640 etc., that can contain commonly used additives like antibiotics, for example streptomycin and penicillin in the concentrations usually employed.

The cells obtainable by this method can be used to prepare medicaments that modulate the immune system or immune response in a mammal, particularly a human, in controlled manner. Therefore the cells as well as the use thereof are part of the invention.

Moreover, it was found that umbilical cord cells (UCC) can be isolated according to the invention by the following method which comprises:

a) isolating umbilical cord from human placenta
b) washing the umbilical cord of step a) to remove contaminants,
c) cutting the umbilical cord of step b),
d) placing the umbilical cord fragments of step c) in a plate,
e) lefting the umbilical cord fragments of step d) to adherence on the plastic for 12 to 30 hour at 33 to 42° C.
f) adding medium to umbilical cord fragments of step e)

g) changing medium to umbilical cord fragments of step f) every 3 to 7 days, h) collecting UCC explanted from umbilical cord fragments of step f).

The cells obtainable with this method are also useful for therapeutical preparations for modulating the actions of immune cells.

Materials and Methods

Isolation of Cells from the Amnion Mesenchymal Tissue

Human term placentas were obtained from healthy women with informed consent after vaginal delivery or caesarian section and processed immediately. The amnion was manually separated from the chorion, washed extensively in phosphate buffered saline (PBS) (Sigma, St. Louis, USA) containing 100 U/ml penicillin and 100 µg/ml streptomycin (both from Euroclone, Whetherrby, UK), and cut into small pieces. Amnion fragments were incubated at 37° C. for 8 min in PBS containing 2.4 U/ml dispase (Roche, Mannheim, Germany), and then transferred at room temperature for 10 min in RPMI 1640 medium (Cambrex, Verviers, Belgium) supplemented with 10% heat-inactivated fetal bovine serum (FBS) (Sigma), 100 U/ml penicillin, 100 µg/ml streptomycin and 2 mM L-glutamine (Cambrex). Afterwards, the fragments were digested with collagenase (0.75 mg/ml) (Roche) and DNAse (20 µg/ml) (Roche) for approximately 3 h at 37° C. Resulting cell suspensions were gently centrifuged (150 g for 3 min) and the supernatant was filtered through a 100-µm cell strainer (BD Falcon, Bedford, Mass.). Finally, cells were collected by centrifugation at 300 g for 10 minutes.

We refer to these freshly isolated cells from the mesenchymal tissue of the amnion as amniotic mesenchymal tissue cells (AMTC).

Isolation of HLA-DR-Positive and HLA-DR-Negative Cells from AMTC

The separation of HLA-DR-positive (HLA-DR$^+$) cells from fresh preparations of AMTC was performed using the MACS system and direct labelling. Cells were first incubated with anti-HLA-DR microbeads (Miltenyi Biotec, Bergisch Gladbach, Germany) at 4° C. for 20 min. After washing, separation of the HLA-DR+ and HLA-DR-fractions was performed by two subsequent column purifications following manufacturer specifications. The percentage of HLA-DR$^+$ cells in the enriched and depleted fractions was determined by flow cytometry.

Peripheral Blood and T Cells Isolation

Human peripheral blood mononuclear cells (PBMC) were obtained from heparinized whole blood samples or buffy coats donated by healthy subjects after informed consent using density gradient centrifugation (Lymphoprep, Axis Shield, Oslo, Norway).

T lymphocytes were purified from PBMC after plastic adherence for 1.5-2 hours at 37° C. and the selection of T cells was performed by indirect magnetic labelling system using Pan T cell Isolation Kit II (Miltenyi Biotec) according to the manufacturer's instructions. Purity was checked by FACS analysis and higher than 95% of recovered cells were CD3 positive.

Amnion Cultures

Freshly isolated AMTC were plated in 75 cm$^2$ flasks (Corning Inc., Corning, N.Y.) at a density of 4-5×10$^6$ cells/flask in 15 ml of RPMI complete medium composed by RPMI 1640 medium (Cambrex, Verviers, Belgium) added with 10% heat-inactivated fetal bovine serum (FBS) (Sigma), 100 U/ml penicillin, 100 µg/ml streptomycin (both from Euroclone, Whetherrby, UK) and 2 mM L-glutamine (Cambrex). Confluent cells were washed in PBS and then detached with 0.25% trypsin (Sigma) before being re-plated in RPMI complete medium in 75 cm$^2$ flasks at a density of 3×10$^6$ cells/flask.

For supernatant collection, AMTC were plated in 24-well plates at 1×10$^6$ cells/well, in a final volume of 1 ml of RPMI complete medium. Each day for 6 days, the supernatant was collected, centrifuged, filtered using a 0.2 µm sterile filter and supplemented with 10% of heat-inactivated fetal bovine serum (FBS, Sigma) before being frozen at −80° C. until usage.

Amnion Cell Co-Culture with PBMC or Purified T Cells

To study the effects of amniotic mesenchymal cells (AMTC) and their subpopulations (AMTC HLA-DR-negative and -positive) on T lymphocyte proliferation, 1.6×10$^5$ unfractionated, HLA-DR-negative or HLA-DR-positive AMTC were plated in RPMI complete medium and left to adhere overnight. The next day, the cells were irradiated (3000 cGy) and an equal number of PBMC or purified T cells were added. All cultures were carried out in triplicate, using round-bottom 96-well tissue culture plates (Corning Inc., Corning, N.Y.), in a final volume of 200 µl of RPMI complete medium. Proliferation of T cells and PBMC was assessed after 2-3 and 5 days by adding [$^3$H]-thymidine (1 µCi/well, INC Biomedicals, Irvine, Calif.) for 16-18 hours. Cells were then harvested with a Filtermate Harvester (Perkin Elmer, Life Sciences, Zaventem, Belgium), and thymidine incorporation was measured using a microplate scintillation and luminescence counter (Top Count NXT, Perkin-Elmer).

Effect of AMTC on Mixed Lymphocyte Reaction

For MLR with AMTC in cell-cell contact, 1×10$^5$ fresh or cultured AMTC were plated in RPMI complete medium and left to adhere overnight. The next day, AMTC were gamma-irradiated (3000 cGy) and an equal number of "responder" PBMC or T cells were added together with an equal number of gamma-irradiated (3000 cGy) allogeneic "stimulator" PBMC. MLR without AMTC were used as controls. Experiments with different AMTC concentrations were performed by maintaining constant the number of PBMC (1×10$^5$) and decreasing amount of AMTC added to obtain ratios of PBMC:AMTC of 1:1, 1:0.4, 1:0.2, 1:0.1 and 1:0. All cultures were carried out in triplicate, using round-bottom 96-well tissue culture plates (Corning Inc., Corning, N.Y.), in a final volume of 200 µl of RPMI complete medium.

For mixed lymphocyte reactions with segregated AMTC, transwell chambers with 0.4 µm pore size membrane (Corning) were used to physically separate the lymphocytes from the AMTC. PBMC (1.5×10$^6$) or T cells (1.5×10$^6$) were co-cultured with equal numbers of gamma-irradiated (3000 cGy) allogeneic PBMC in a 24-well tissue culture plate (Corning) in a final volume of 1 ml of RPMI complete medium. An equal number of fresh or cultured AMTC in a volume of 300 µl of RPMI complete medium was then added to the transwell chambers. Experiments were performed with different AMTC numbers and maintaining constant the number of PBMC to obtain ratios of PBMC:AMTC of 1:1, 1:0.4, 1:0.2, 1:0.1 and 1:0.

MLR were also performed in the presence of supernatant collected from AMTC cultured for a variable number of days. All cultures were carried out in triplicate using round-bottom 96-well tissue culture plates (Corning), with the addition of 150 µl of AMTC "conditioned" medium in a final volume of 200 µl.

In all cases, cell proliferation was assessed after 5 days of culture by adding 1 µCi/well (96-well tissue culture plates) or 5 µCi/well (24-well tissue culture plates) of [$^3$H]-thymidine (INC Biomedicals) for 16-18 hours. Cells were then harvested with a Filtermate Harvester (Perkin Elmer, Life Sciences, Zaventem, Belgium), and thymidine incorporation was measured using a microplate scintillation and luminescence counter (Top Count NXT, Perkin-Elmer).

Effect of AMTC on CD3/CD28-Stimulated PBMC or T Cells

To study the effect of AMTC and their sub-populations (AMTC HLA-DR-negative and -positive) on CD3/CD28-stimulated PBMC or T cells, fresh or cultured unfractionated, HLA-DR-negative or HLA-DR-positive AMTC ($1.6\times10^5$) were seeded in 96-well plates and left to adhere overnight. The next day, AMTC were gamma-irradiated (3000 cGy) and an equal number of PBMC or purified T cells were added and activated with soluble 1 µg/ml of anti-CD3 monoclonal antibody (Orthoclone OKT3, Orthobiotech, NJ, USA) either alone or in combination with 7 µg/ml soluble anti-CD28 (clone CD28.2, Biolegend, San Diego, Calif.). Cultures were carried out in triplicate, using round-bottom 96-well tissue culture plates (Corning), in a final volume of 200 µl of RPMI complete medium.

For proliferation assays using transwell chambers, $1.5\times10^6$ PBMC or purified T cells were cultured in 24-well plates and stimulated by anti-CD3 monoclonal antibody anti-CD28 as described above. Cultures were carried out in a final volume of 1 ml of RPMI complete medium. AMTC ($1.5\times10^6$) were seeded in the inner transwell chamber in a volume of 300 µl of RPMI complete medium.

Cellular proliferation was assessed after 2-3 days of culture by adding [$^3$H]-thymidine for 16-18 hours and assessing incorporation of radioactivity as described above.

Re-Stimulation of Lymphocytes Following Culture with AMTC

PBMCs ($1.5\times10^6$) were incubated with equal numbers of gamma-irradiated (3000 cGy) allogeneic PBMCs in 24-well tissue culture plates (Corning) in a final volume of 1 ml of RPMI complete medium. Equal numbers of gamma-irradiated (3000 cGy) AMTC were added in a volume of 300 µl of RPMI complete medium in the transwell chambers (Corning). After 5 days of culture, the transwell chambers containing AMTC were removed. Lymphocytes which had been cultured in the presence of AMTC via transwell were then collected, washed twice in phosphate buffered saline containing 100 U/ml penicillin and 100 µg/ml streptomycin, and re-cultured with the original or third party PBMC stimulators. Lymphocyte proliferation was assessed after 5 days of culture as described above.

Flow Cytometry Analysis

For evaluation of cell phenotype, cell suspensions were incubated for 20 minutes at 4° C. with fluorescein isothiocyanate (FITC) or phycoerythrin (PE)-conjugated antibodies specific for human CD1a (clone HI149), CD3 (clone UCHT1), CD11b (clone ICRF44), CD14 (cloneMφP9), CD16 (clone 3G8), CD45 (clone HI30), CD80 (clone L307.4), CD83 (clone HB15e), CD86 (clone 2331) and HLA-DR (clone TÜ36), or iso-type controls IgG1 (clone X40), IgG2a (clone X39), IgG2b (clone MG2b-57). All monoclonal antibodies were obtained from BD Biosciences (San Jose, Calif.) except for isotype control IgG2b that was obtained from Biolegend (San Diego, Calif.). Samples were analysed with a FACSCalibur and the CellQuest Software (BD Biosciences).

Immunohistochemistry Analysis

Immunohistochemical studies were performed on formalin-fixed and paraffin-embedded sections using the Super Sensitive™ IHC Detection System (BioGenex) with monoclonal antibodies specific for HLA-DR (Novocastra, clone LN-3) diluted 1:200, CD68 (DakoCytomation, clone KP1) diluted 1:100, and CD45 RO (DBS, clone A6) diluted 1:100.

The sections were deparaffinized in xylene and rehydrated in graded ethanol. The endogenous peroxidase activity was blocked using 3% hydrogen peroxide solution.

The primary antibody was then applied for 1 hr at room temperature followed by incubation with the Super Enhancer™ Reagent for 20 min and then application of Poly-HRP Reagent for 30 min at room temperature. DAB-3,3'-diaminobenzidine was used as the chromogen, and hematoxylin for counterstaining.

RFLP Analysis

DNA was extracted from placental deciduas, unfractionated and HLA-DR-positive AMTC using the Nucleospin Tissue Kit II (BD Biosciences) according to the manufacturer's instructions. PCR analysis of the minisatellite polymorphic locus D1S80 was then performed using an ABI 9700 Thermal Cycler (Applied Biosystems, Foster City Calif., USA) and GoTaq DNA Polymerase reagents (Promega, Madison, USA) as previously described (Maddalena Soncini, manuscript submitted March 2007). The PCR mixtures contained 200 µM dNTPs and 25 pmol of each primer in a total volume of 50 µl. The cycling conditions consisted of an initial denaturation step at 95° C. for 10 min, followed by 35 cycles of 95° C. for 15 s, 66° C. for 45 s, and 72° C. for 1 min. PCR products were then separated by electrophoresis on 2.5% agarose gel (Bio-rad, Hercules, Calif.), which was then stained with ethidium bromide.

Statistical Analysis

The Student's t test was used for statistical analysis. Differences were considered statistically significant at P value less than 0.05.

Results

AMTC Inhibit Mixed Lymphocyte Reaction

Figure 2A:
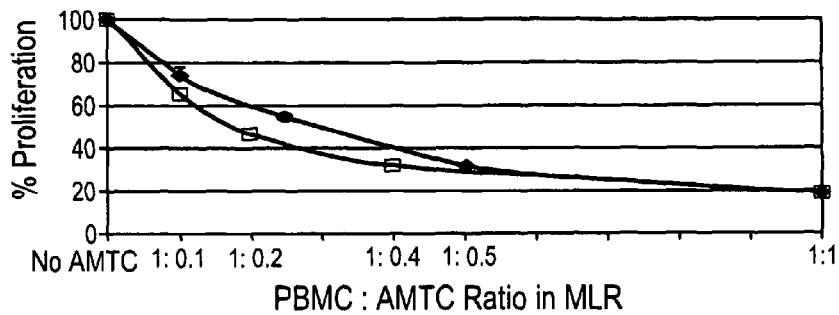
FIG. 2A is a graph showing AMTC inhibitory conditions in MLR where responder PBMC were incubated with irradiated allogeneic stimulator PBMC.

We set out to study the effects of AMTC on classic MLR cultures as a model of allogeneic lymphocyte responses. We found that exposure of PBMC or isolated T cells to AMTC reproducibly inhibited MLR-induced cell proliferation both through cell-cell contact and in transwell system (FIG. 1). The inhibitory effect was dependent on the amount of AMTC present in the co-cultures, with the strongest effects observed at a ratio AMTC:"responder" cells of 1:1, both in the cell-cell contact and transwell experiments (FIG. 2A).

Figure 2B:
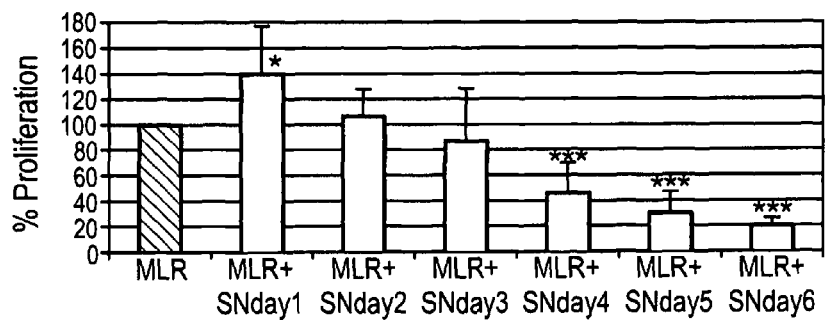
FIG. 2B is a graph showing AMTC inhibitory conditions in MLR, where MLR were performed alone (black bar) or in the presence of supernatants (SN) from AMTC cultures (white bars).
Figure 2C:
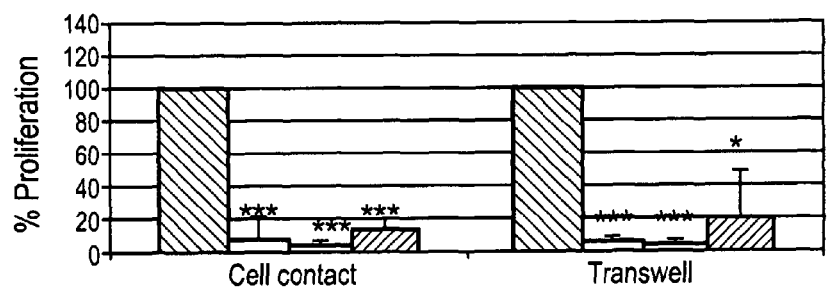
FIG. 2C is a graph showing AMTC inhibitory conditions in MLR, where MLR were performed alone (black bar) or in the presence of AMTC at passage 1 (white bar), passage 2 (gray bar), or passage 3 (hatched bar).

The inhibitory effect observed in the transwell system was suggestive of soluble inhibitory factor(s). This possibility was confirmed by the observation that MLR inhibition was induced also by the addition of FCS supplemented supernatant collected from cultured AMTC. The inhibitory factor(s) seemed to accumulate with time in the AMTC conditioned medium, since the inhibition effects were observed only in cultures added with supernatant obtained from AMTC cultured for more than 3 days and increased gradually with the length of AMTC culture (FIG. 2B); similar results were obtained with essential and non essential amino acid plus FCS supplementation of AMTC culture supernatants (data not shown). The inhibitory potential of AMTC was maintained up to three AMTC culture passages in experiments with both cell-cell contact or transwell co-culture (FIG. 2C).

Figure 2D:
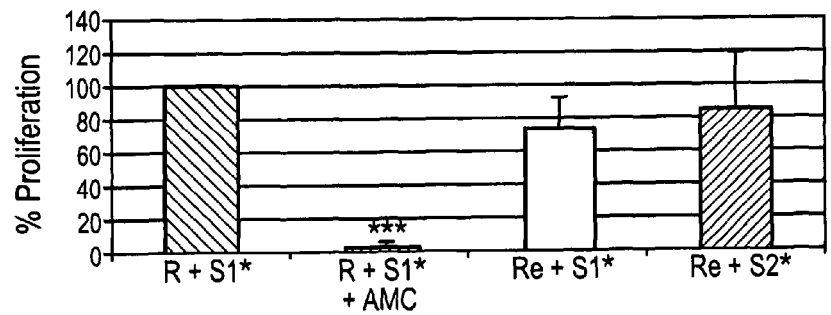
FIG. 2D is a graph showing AMTC inhibitory conditions in MLR, where MLRs were set up between responder PBMC (R) and equal numbers of allogeneic stimulator PBMC (S1*), with and without the addition of an equal number of AMTC in a transwell chamber.

Interestingly, "responder" cells previously exposed to AMTC in the transwell system were able to proliferate in new MLR cultures against either the original or a new allogeneic PBMC "stimulator" cells (FIG. 2D) suggesting that the inhibitory effect is only transient and that AMTC do not induce T cells death.

AMTC Inhibit Proliferation Induced by CD3 and CD28 Activation

To better define the observed cell proliferation inhibition, we tested the effects of AMTC on PBMC and purified T cells stimulated with anti-CD3 with or without anti-CD28.

Figure 3A:
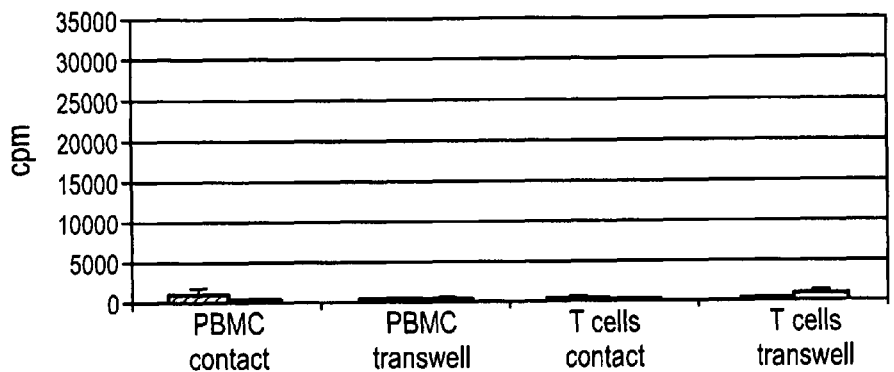
FIG. 3A is a graph showing the effect of AMTC on unstimulated and CD3, CD3/CD28 stimulated PBMC and T cells, where PMBC and T cells were cultured alone.
Figure 3B:
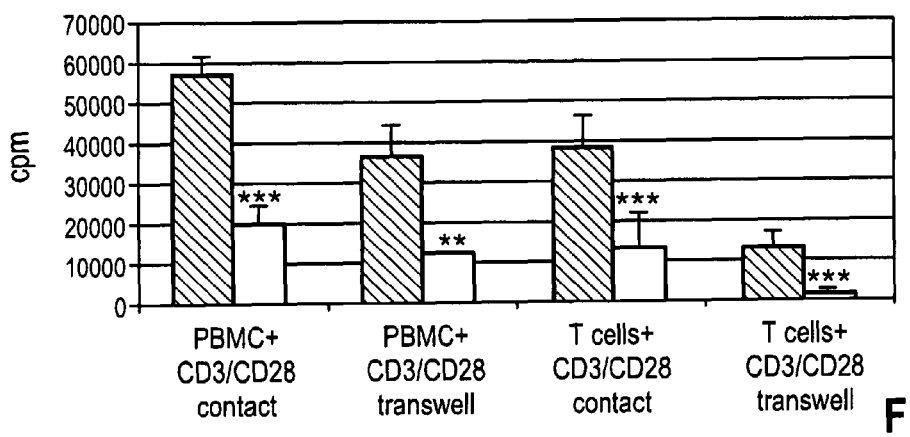
FIG. 3B is a graph showing the effect of AMTC on unstimulated and CD3, CD3/CD28 stimulated PBMC and T cells, where PMBC and T cells were stimulated with anti-CD3 plus anti-CD28 antibody.
Figure 3C:
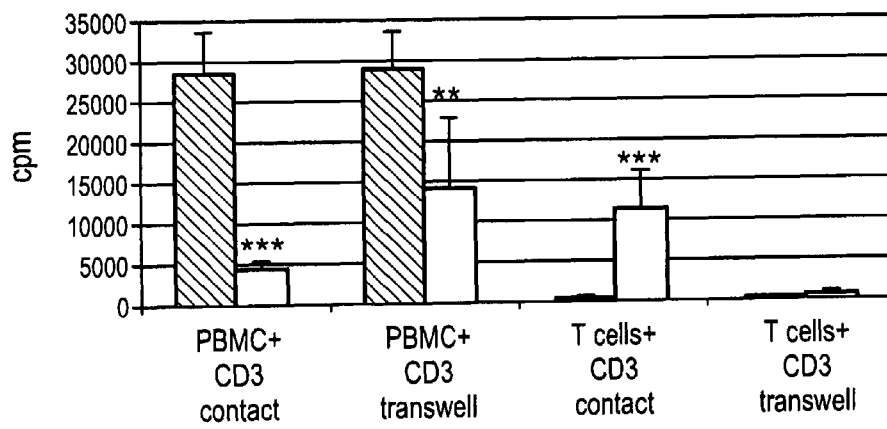
FIG. 3C is a graph showing the effect of AMTC on unstimulated and CD3, CD3/CD28 stimulated PBMC and T cells, where PMBC and T cells were stimulated with anti-CD3 antibody alone.

In the absence of TcR stimulation, AMTC did not induce proliferation responses in neither PBMC nor purified T cells (FIG. 3A), thus indicating that these cells do not induce allogeneic responses. AMTC, however, inhibited PBMC and T cell proliferation induced by anti-CD3/anti-CD28 stimulation (FIG. 3B) either when co-cultured in cell-cell contact or in the transwell system. In addition, AMTC inhibited PBMC proliferation induced by anti-CD3 stimulation (FIG. 3C). Surprisingly, however, the anergy of purified T cells to stimulation with anti-CD3 was overcome by the addition of AMTC. This proliferative effect was observed only in the cell-cell contact setting and not in the transwell experiments (FIG. 3C). Stimulation of AMTC with anti-CD3 did not induce cell proliferation (data not shown).

Determination of AMTC Subpopulations

To investigate the basis of the co-stimulatory properties of AMTC in the presence of purified T cells, we performed flow cytometry analysis of these cells.

Figure 4A:
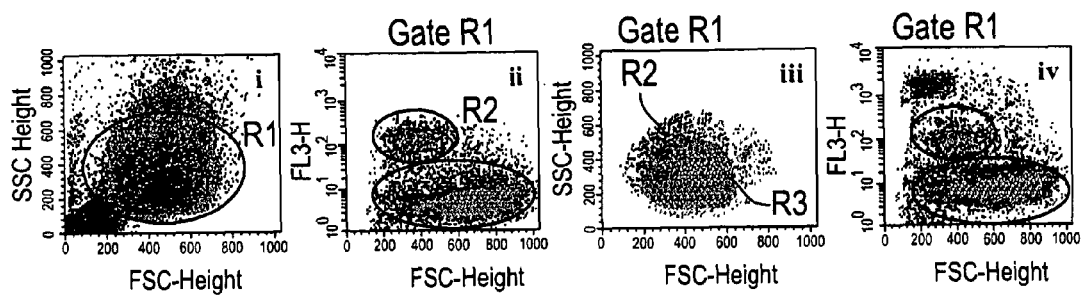
FIGS. 4A-C show a representative FACS analysis of cells isolated from the mesenchymal amniotic region.

While performing routine exclusion of propidium iodide-positive cells from FSC/SSC-gated AMTC (R1), we observed the presence of two distinct populations (R2 and R3) with different autofluorescence characteristics (FIG. 4Ai-iii). We confirmed the presence of these two different populations in all placenta preparations we analyzed. The percentage of the population with high autofluorescence (R2) varied with a range from 5 to 12% of AMTC.

Figure 4B:
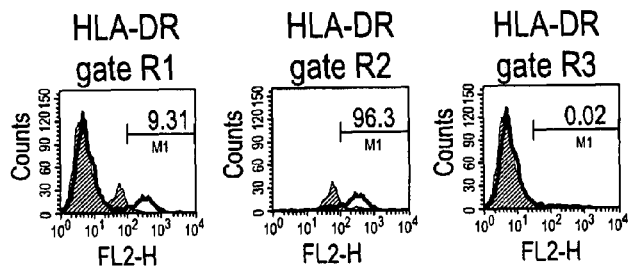

To begin to characterize these two different populations, we performed a series of immunophenotypic studies which showed that cells in gate R2 were higher than 90% positive for HLA-DR, while the remaining subpopulation (R3) was HLA-DR negative (FIG. 4B). Absence of propidium iodide positivity suggested that these cells were viable (FIG. 4A iv).

Figure 4C:
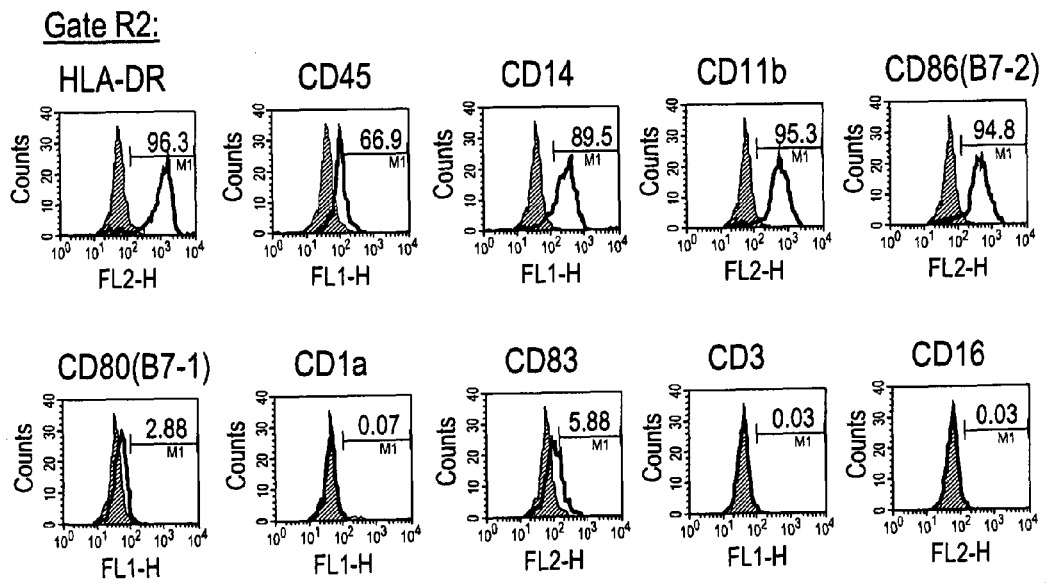
Figure 5A:
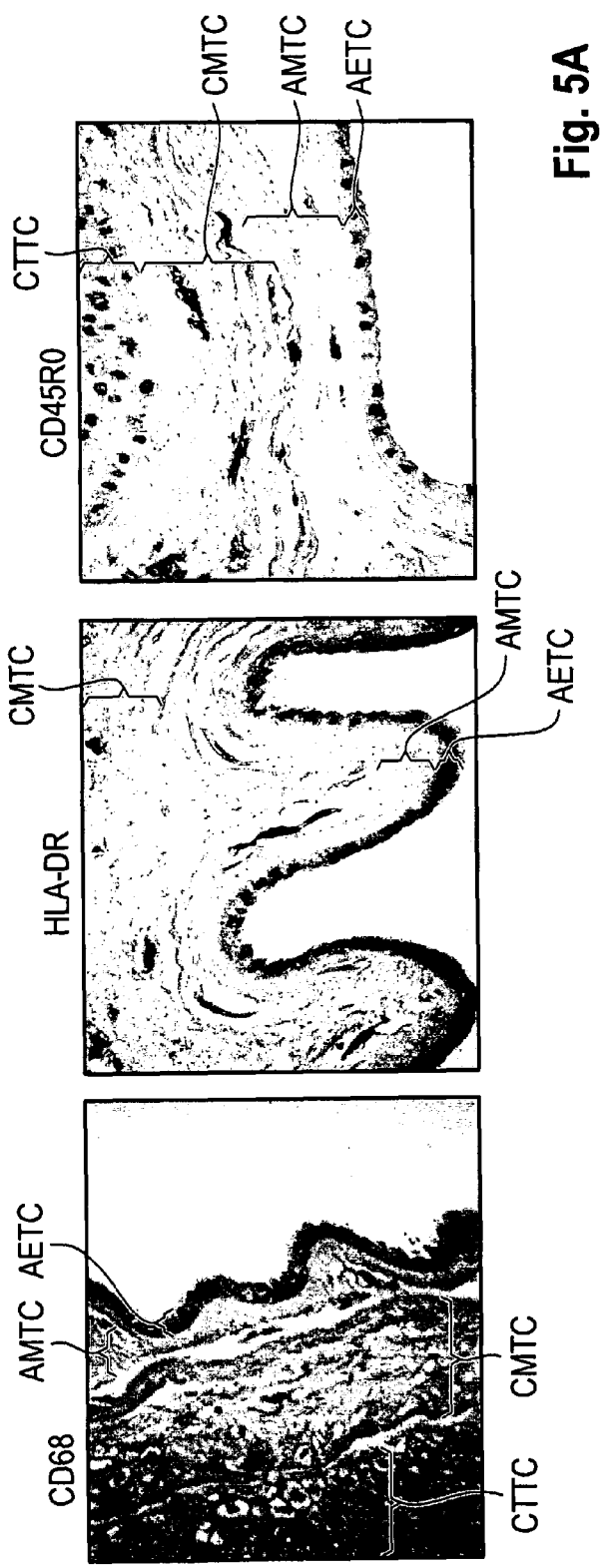
FIG. 5A shows a determination of subpopulations present in the mesenchymal amniotic region by immunohistochemical staining of representative paraffin sections of term placental amniotic and chorionic membranes.
Figure 5B:
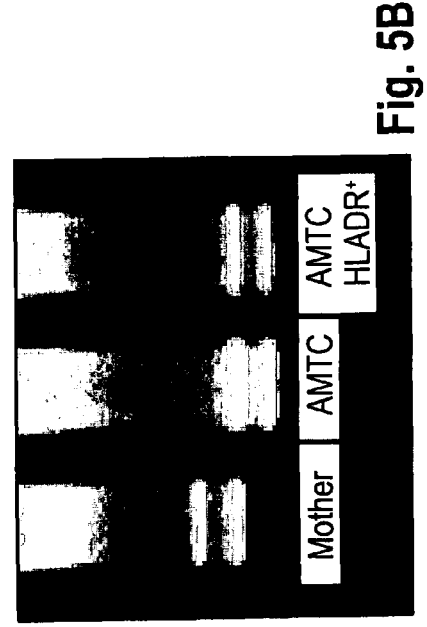
FIG. 5B shows a determination of subpopulations present in the mesenchymal amniotic region by RFLP analysis of DNA extracted from HLA-DR$^+$ AMTC.

Further analysis of R3 cells, showed expression of the hematopoietic marker CD45 and the monocytic antigens CD14, CD11b, CD86 in the absence of dendritic (CD1a, CD83) and T/NK (CD3, CD16) cell markers (FIG. 4C). Interestingly the HLA-DR$^+$ cells showed strong positivity for the costimulatory molecule CD86 and the absence of CD80. In addition, immuno-hystochemical staining of placenta sections confirmed the presence of CD45$^+$, HLA-DR$^+$, CD68$^+$ cells in the stromal region of amnion (FIG. 5A). Molecular analysis of DNA obtained from HLA-DR$^+$ AMTC using highly polymorphic RFLPs allowed us to determine the fetal origin of such cells (FIG. 5B).

Effects of AMTC DR$^+$ and AMTC DR$^-$ on T Cell Proliferation

Figure 6A:
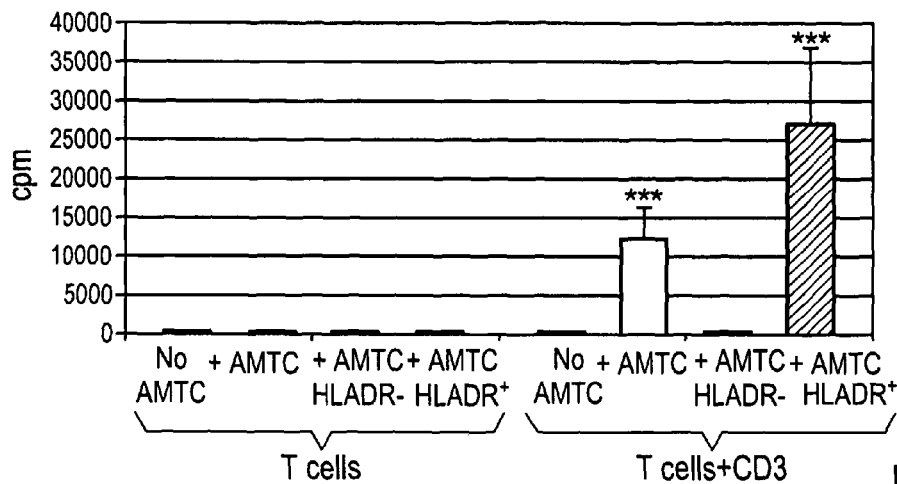
FIG. 6A is a graph showing the effect of cells isolated from mesenchymal amniotic region on CD3 stimulated T cells, where purified T cells were cultured alone or in direct contact with unfractionated, HLA-DR-negative or HLA-DR positive AMTC, with or without anti-CD3.
Figure 6B:
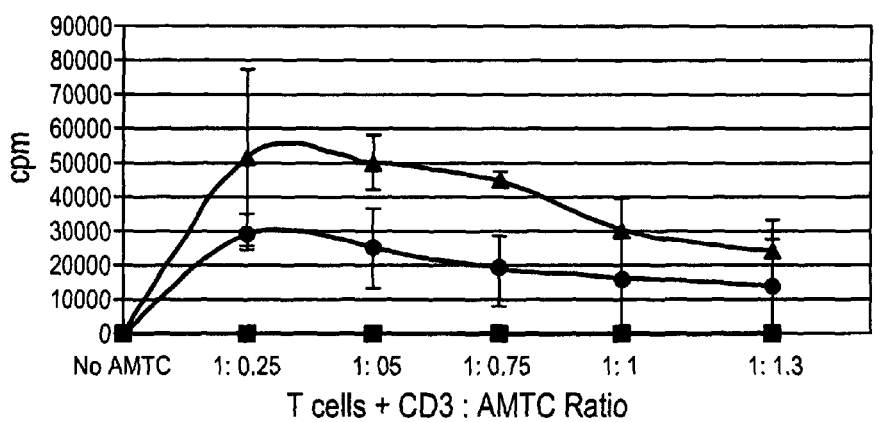
FIG. 6B is a graph showing the effect of cells isolated from mesenchymal amniotic region on CD3 stimulated T cells, where purified T cells, stimulated with anti-CD3, were cultured alone or in direct contact with increasing concentrations of total AMTC (●), HLA-DR-negative (■) or HLA-DR-positive (▲) AMTC.

We hypothesized that HLA-DR$^+$ amniotic cells played a role in the co-stimulation of T cell proliferation observed in the presence of AMTC. To test this hypothesis, we obtained HLA-DR$^+$ enriched (>90% HLA-DR-positive), and depleted (<5% HLA-DR-positive) AMTC fractions. Both HLA-DR$^+$ and HLA-DR" AMTC fractions did not induce allogeneic T cell responses. However, in contrast to the HLA-DR$^-$ AMTC, HLA-DR$^+$ and unfractionated AMTC induced marked T cell proliferation in the presence anti-CD3 stimulation (FIG. 6A). We also observed a dose dependent effect on T cell proliferation by both unfractionated and HLA-DR$^+$ AMTC (FIG. 6B). These results suggest that the HLA-DR$^+$ AMTC population is involved in T cell proliferation in the presence of anti-CD3 stimulation.

Figure 6C:
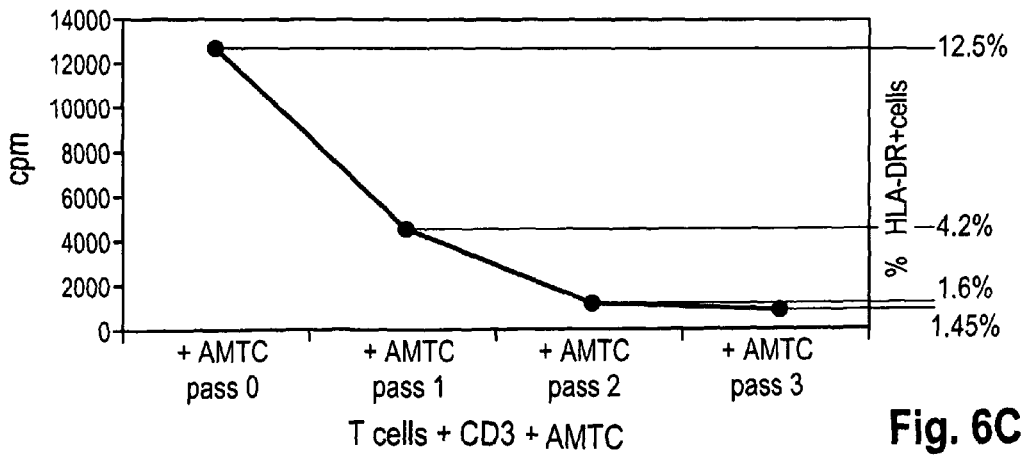
FIG. 6C is a graph showing the effect of cells isolated from mesenchymal amniotic region on CD3 stimulated T cells, where purified T cells, stimulated with anti-CD3, were cultured alone or in direct contact with total AMTC cultured for different numbers of passages.

We observed that HLA-DR$^+$ AMTC cells decrease markedly in numbers during in vitro AMTC culture passages, with a percentage approximately of only 0.5-2% remaining after three passages. Such decline correlated with a reduction of the co-stimulatory effects of AMTC on T-cells prior stimulated by anti-CD3 (FIG. 6C).

Figure 7A:
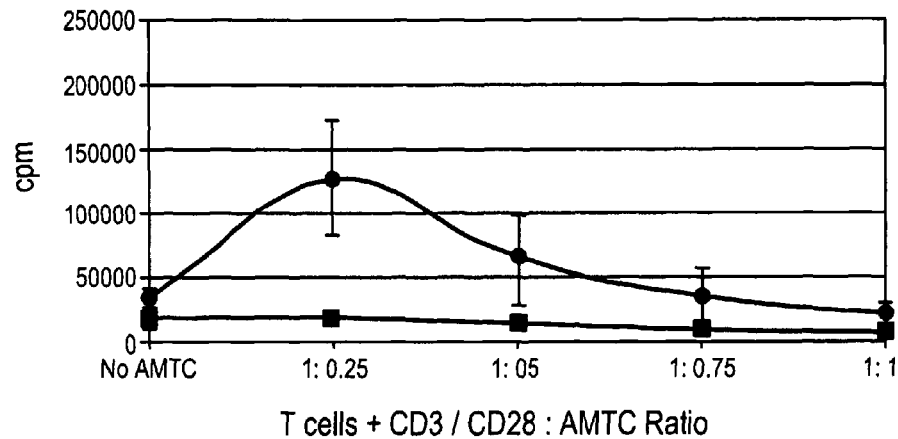
FIG. 7A is a graph showing the effect of amnion mesenchymal cells on purified T cells stimulated by CD3 plus CD28 where purified T-cells, stimulated with anti-CD3 and anti-CD28, were cultured alone or in the presence of increasing concentrations of total AMTC, in either direct contact (●) or in transwell chambers (▲).

In transwell experiments with purified T cells activated with anti-CD3 and anti-CD28 antibodies, AMTC always inhibited T cell proliferation in a dose-dependent manner, as shown in FIG. 7A. In contrast, in cell-cell contact conditions, AMTC inhibited T-cell proliferation when added at higher concentrations (T cells:AMTC ratio of 1:1 or 1:1.3), while they induced T-cell activation when added at lower concentrations (FIG. 7A).

Figure 7B:
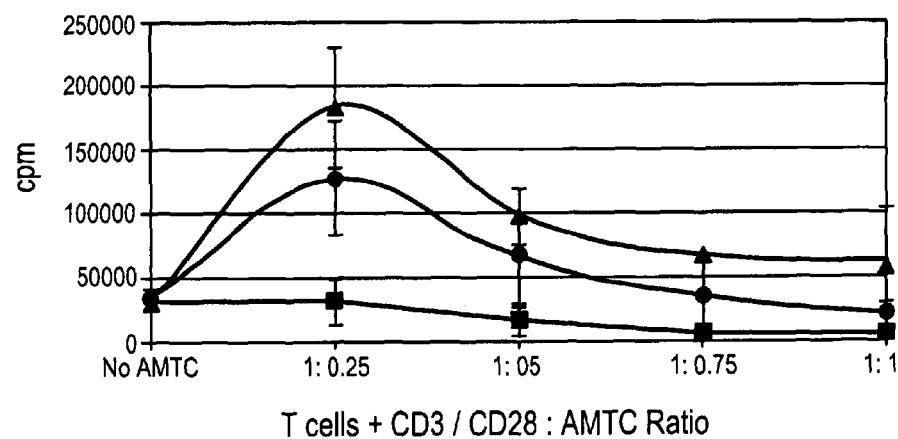
FIG. 7B is a graph showing the effect of amnion mesenchymal cells on purified T cells stimulated by CD3 plus CD28 where purified T cells, stimulated with anti-CD3 and anti-CD28, were cultured alone or in direct contact with increasing concentrations of total AMTC (●), HLA-DR-negative (■), or HLA-DR-positive (▲) AMTC.

To characterize these findings, we performed cell-cell contact experiments with purified T cells activated with anti-CD3 and anti-CD28 and co-cultured with irradiated unfractionated, HLA-DR$^+$ and HLA-DR$^\oplus$ AMTC. As shown in FIG. 7B, the HLA-DR$^+$ AMTC induced T cell proliferation, whereas the HLA-DR$^-$ AMTC fraction had an inhibitory effect in a dose dependent manner. Interestingly, unfractionated AMTC showed both activation and inhibition of cell proliferation, which was dependent on the dose of AMTC included in the culture.

Discussion

Recently it was reported that the mesenchymal region of amnion from human term placenta contains cells with phenotypical, functional and immunomodulatory characteristics similar to those described for MSC derived from other sources such as BM, adipose tissue and cord blood. [Parolini, 2006 #64; Fukuchi, 2004 #95; Alviano, 2007 #93; Portmann-Lanz, 2006 #48; Chang, 2006 #94].

The present application now provides the immunomodulatory properties of different cell subpopulations isolated from the mesenchymal tissue of the amniotic membrane with a focus on their effect on the proliferation of T cells stimulated with allogeneic target cells (MLR) or via T cell receptor engagement.

Unfractionated AMTC are capable to inhibit MLR T cell proliferation not only when cultured in direct cell contact with "responder" cells, but also when separated from them by a transwell membrane. The inhibition effects were more pronounced when increasing numbers of AMTC were added to the cultures, suggesting a dose-dependent effect. The finding that inhibition of T cell proliferation was induced by AMTC in the transwell system suggests that a soluble factor is implicated in such phenomenon. This hypothesis is supported also by our findings that T cell proliferation was inhibited by the addition of AMTC culture supernatant.

The nature of such transferable inhibitory factor remains unknown. However, it is of note that soluble factors, even though not unequivocally identified, have been implicated in the anti-proliferative capabilities of MSC of other origins such as bone marrow and adipose tissue [Di Nicola, 2002 #11; Djouad, 2003 #5; Tse, 2003 #47; Meisel, 2004 #9, Jiang, 2005 #45; Rasmusson, 2005 #25; Nauta, 2006 #42], although the need for cell-cell contact and/or additional cell types (monocytes, dendritic cells) in such settings remains an area of debate [Krampera, 2003 #12; Potian, 2003 #15; Beyth, 2005 #38].

Particularly the identification of subpopulations expressing the leukocyte HLA-DR molecules is provided. The mesodermal region of amnion is considered to be avascular and therefore presence of hematopoietic cells is not expected. However, FACS analysis of freshly isolated AMTC revealed a defined HLA-DR-positive subpopulation co-expressing the monocyte-specific markers, CD14, CD11b and CD86. The presence of cell with monocytic immunophenotype was confirmed by immunohistochemistry of whole placenta samples and PCR analysis proved the fetal origin of these cells. Although previous studies have reported on the presence of HLA-DR$^+$ cells in the mesenchymal region of the amniotic membrane [Sutton, 1986 #83; Sutton, 1983 #84; Bulmer, 1988 #85], expression of MHC II antigens has generally be reported to be low or absent on cells isolated from the amnion mesenchymal region [Portmann-Lanz, 2006 #48]. The discrepancy between these previous reports and the present findings can be explained by the use of different cell isolation protocols. In addition, given the rapid reduction of the HLA-DR+ cells that was observed in cultured AMTC, it is also possible that the timing of analysis of MHC II expression can account for some of the findings described in the literature. It is important to note that contrasting reports on the presence of HLA-DR+ and CD45+ cells exist also for the BM-MSC field [Potian, 2003 #15; Krampera, 2003 #12; Kern, 2006 #69].

It was observed that unfractionated and purified HLA-DR+ and HLA-DR" AMTC failed to induce T cell proliferation in the absence of additional stimuli. The lack of T cell responses against HLA-DR+ allogeneic cells may appear surprising. However, previous studies have shown that exposure to INF-gamma can induce high level of expression of MHC II on BM-MSC which remain unable to induce T cell proliferation [Tse, 2003 #47; Klyushnenkova, 2005 #92].

Interestingly, AMTC induced strong proliferation in CD3-stimulated T cells when co-cultured in direct cell contact. This effect was even stronger when the HLA-DR+ AMTC subpopulation was used, suggesting that these cells are capable of providing costimulatory signals. It was found that the prevalence of HLA-DR+ AMTC decreased with in vitro culture, which correlated with a reduction of the stimulating properties of unfractionated AMTC. In contrast to their inhibitory function, the co-stimulatory of AMTC effect appears to require direct cell contact since it was not observed in the transwell system. The detection of the CD86 molecule on the HLA-DR+ AMTC suggests that the CD86/CD26 costimulatory pathway may be involved in the activation of T lymphocyte proliferation induced by AMTC in cells that received TcR stimulation.

A significant AMTC dose-dependent phenomenon was observed in proliferation experiments using purified T "responder" cells and TcR engagement with CD3 and CD28 as stimulation. At low AMTC:T cell ratios, AMTC induced T cell proliferation. The stimulatory effect was not observed when AMTC were cultured in the transwell system indicating the need of cell contact for this phenomenon to occur. Importantly, it could be demonstrated that activation of cell proliferation is associated with the presence of HLA-DR+ AMTC. These observations are reminiscent of previous puzzling findings indicating that low ratios of human MSC to T cells can augment "responder" cell proliferation rather than suppressing it [Le Blanc, 2003 #7; Di Nicola, 2002 #11].

In summary, the present invention teaches that unfractionated AMTC can inhibit T cell proliferation with features that are very similarly to that observed in MSC of various origins. Additionally, a HLA-DR+ fraction of AMTC of fetal origin and with immunophenotypic characteristics similar to human monocytes has been identified that is unable to induce proliferation unless T cells are primed by TcR engagement with anti-CD3. The histological determination of this cells in in the amniotic membrane and their peculiar distribution in "sentinel" arrangements makes us speculate that they may play a role in the fetal maternal tolerance homeostasis. If correct, this hypothesis may implicate in this critical process a region of the placenta (the amnion) located internally to the trophoblast and the maternal deciduas that have generally attracted investigators' attention to date.

Furthermore, these findings may help to reconcile the current debate both on the presence of HLA-DR+ cells, which remains a controversial issue in MSC in general [Kern, 2006 #69], and also the paradoxical results that have been obtained after transplantation of BM-MSC. For example, allogeneic BM-MSC are used in clinical trials to control GvHD [Le Blanc, 2004 #100], however, in murine BMT models, coin-fusion of allogeneic BM and BM-MSC induces a memory T cell response resulting in cell graft rejection [Nauta, 2006 #34]. If a population of HLA-DR+ cells exists within BM-MSC, these cells may account for these opposite immunomodulatory functions, as we have observed.

Further studies are warranted to understand if immunomodulatory functions of AMTC and their possible counterpart in MSC from other tissues can be exploited therapeutically to modulate the outcome of tissue therapies or pregnancy pathologies caused by problems of the fetal-maternal interface. The reliable procedures to obtain such cells, that are described here, will facilitate these important tasks.

This study was supported in part by grants from Fondazione Cariplo, Bando 2004, Fondazione Cariplo Progetto Nobel 2006.

In a further embodiment cells derived from amniotic and/or chorionic fetal membranes of placenta are used for the treatment of lung fibrosis.

It is an further object of the present invention to use cells or cell preparations as described above for preparing a medicament for treating lung fibrosis.

Surprisingly it has been found that the cells as described above have an influence on lung fibrosis. It was found that both allogeneic and xenogeneic transplants of cells can reduce fibroblast proliferation and collagen deposition when administered to the lung. The administration can be carried out for example intratracheal, intra-jugural, intrabronchial or intrapulmonary. It was found that the cells have an anti-inflammatory effect and can treat and/or prevent lung injuries like lung fibrosis.

Lung fibrosis was induced in mice by bleomycin treatment, as previously described (Ortiz et al 1999). The effect of cells derived from the fetal membranes (amnion and chorion) of either human term placenta (xenotransplantation), or placenta from another strain of mouse (allogeneic transplantation) on the progression of bleomycin-induced lung fibrosis was then studied. Compared to untreated controls, a reduction in fibrosis in animals that received allogeneic and xenogeneic cell transplants, as demonstrated by reduced fibroblast proliferation and collagen deposition was observed.

Methodology:

Xenogeneic cells from the fetal membranes of human term placenta were trans-planted as a mixture of mesenchymal cells (hAMCs+hCMCs) and epithelial cells (hAECs) into mice. The cells were obtained by the isolation protocol outlined above or were obtained by methods already known (Bailo et at 2004, Soncini et al 2007 and Magatti et al. 2007).

Animal model used to study the effects of placenta-derived cells:

Lung fibrosis was induced in C57BL/6 mice through intratracheal instillation of bleomycin, as previously described (Ortiz. et al 1999).

Experiments in which cell therapy was undertaken by transplanting bone marrow-derived mesenchymal cells (Ortiz et al 2003 and Ortiz et al 2007 #) or alveolar type II epithelial cells (Serrano-Mollar et al. 2007) into bleomycin-treated rodents have resulted in a marked reduction in lung inflammation and fibrosis.

However, now for the first time it has been found that lung injuries, like fibrosis can be treated using the cells as described above. The results are demonstrated in FIGS. 8 to 10. It is shown that a reduction in bleomycin-induced lung fibrosis in mice is observed when cells derived from the amniotic and/or chorionic fetal membranes are applied in both a xenogenic setting (human into mice) or an allogeneic setting (between two different strains of mouse). It is an advantage to use the cells provided by the present invention because the source for these cells is readily available.

Route and Dose of Inoculation:

For transplantation or inoculation of both allogeneic and xenogeneic cells the intraperitoneal and intratracheal administration routes were used. It is also possible to administer the cells directly to the lungs, i.e. intrapulmonary, or intrabronchially. In addition, the intra jugular administration route was also used for allogeneic cells. For intra-peritoneal transplantation, mice received $4 \times 10^6$ cells, while $1 \times 10^6$ cells were administered in both intra-jugular and intra-tracheal transplantation experiments.

For human use a dosage in the range of about 10 to $100 \times 10^6$ cells is suitable, preferably in the range of about 20 to $80 \times 10^6$ cells. Dosages outside these ranges may be indicated depending from the subject treated and the disease. The use of allogeneic cells is preferred.

Figure 9:
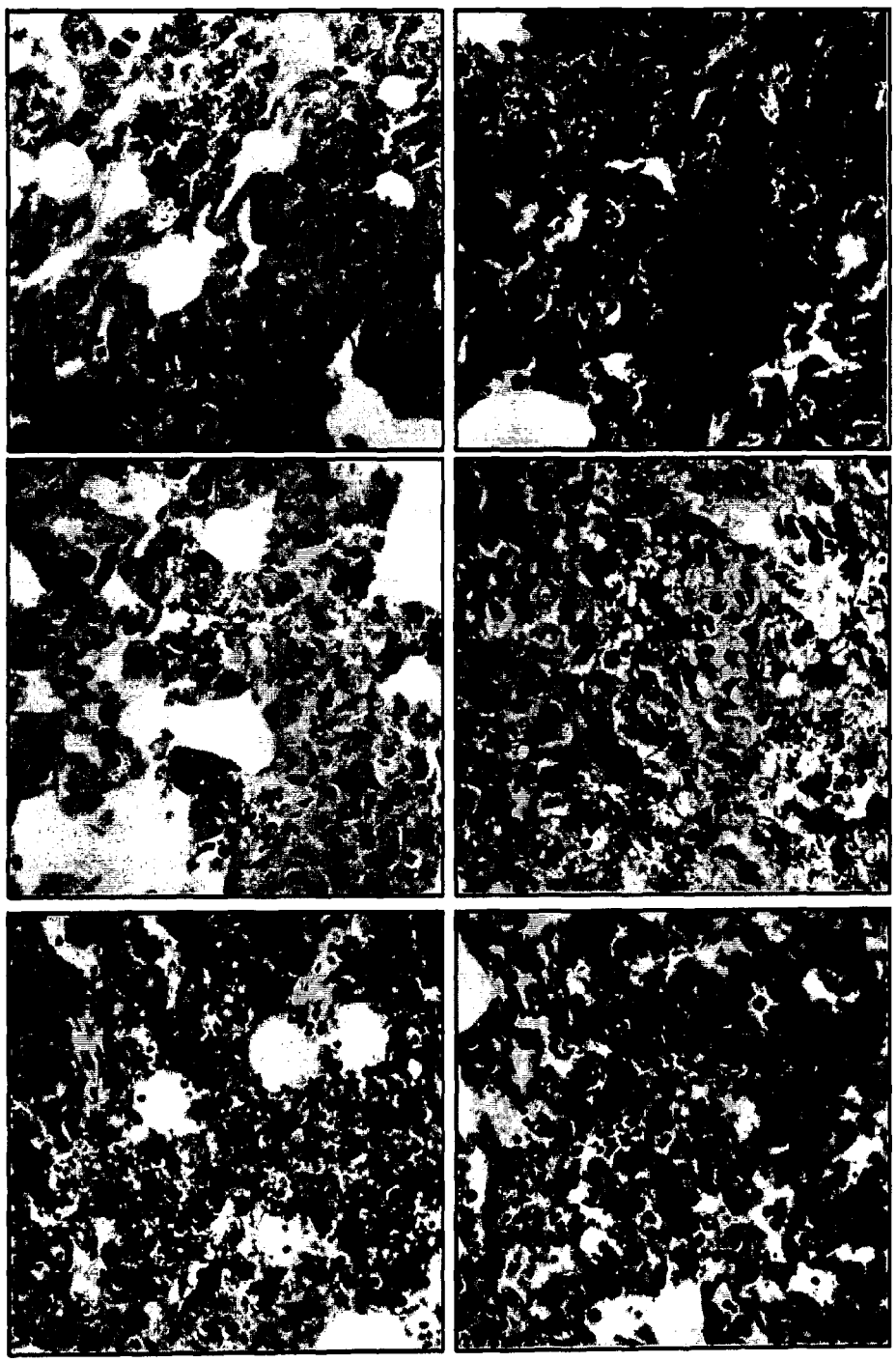
FIG. 9 shows the results of a Masson's staining depicting that transplantation of placenta-derived cells decreases the lung fibrosis induced by bleomycin.
Figure 10:
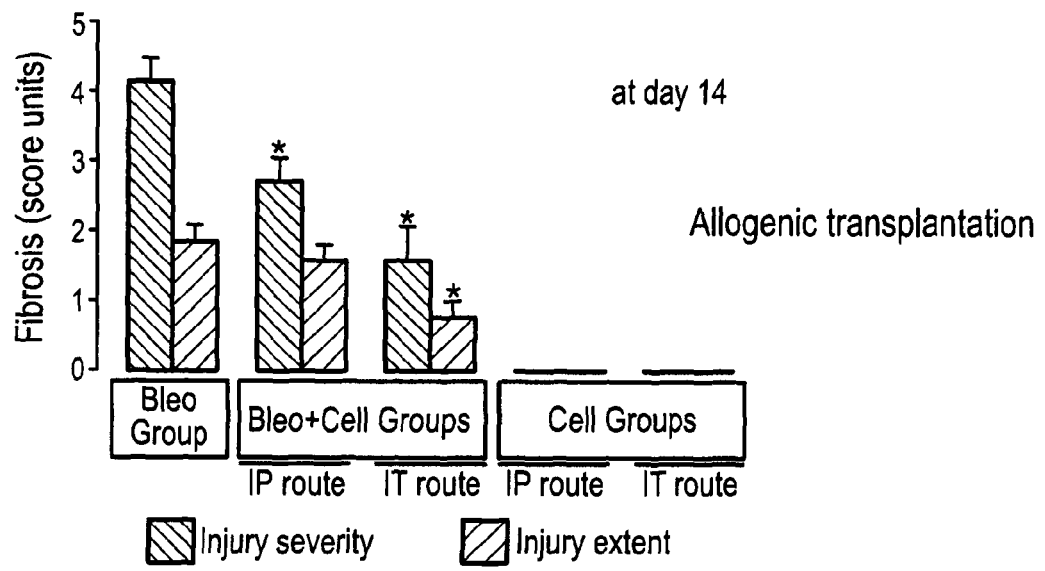
FIG. 10 shows graphs showing the reduction of fibrosis in allogenic and xenogenic transplantation (bleo+cell) versus animals treated with bleomycin (bleo group).
Figure 10:
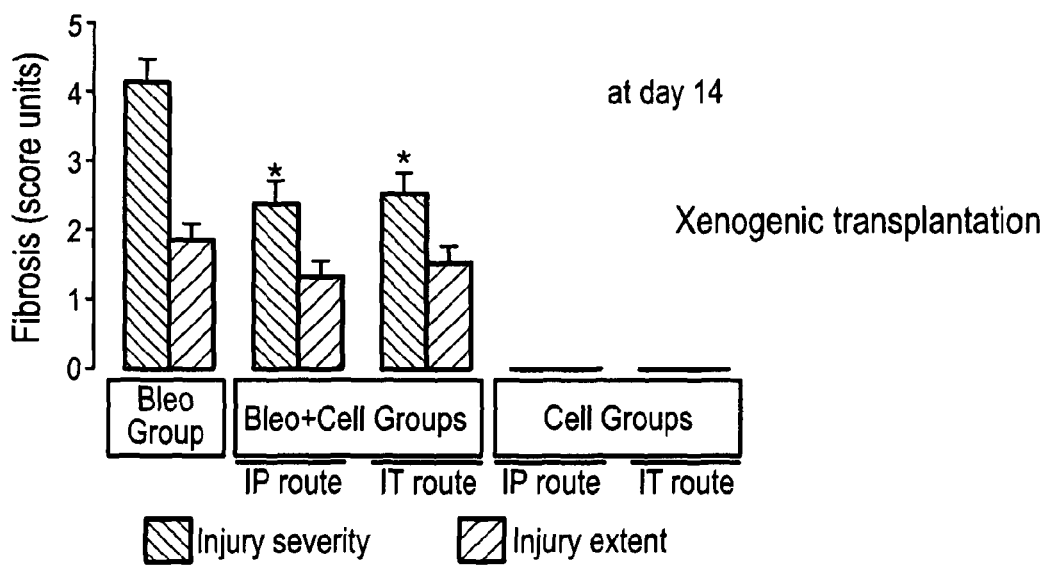

Examination of mouse lungs 14 days after bleomycin treatment revealed that in animals which had received intraperitoneal xenogeneic transplants of human amniochorionic cells, the presence of human cells could be detected, as demonstrated by immunohistochemistry (FIG. 8), while a reduction in fibrosis was also observed, as demonstrated by reduced collagen deposition and fibrosis (FIG. 2). These effects were not observed in bleomycin-treated animals which did not receive xenogeneic cell transplants. FIG. 9 shows a qualitative immunohistochemistry image, while FIG. 10 shows a quantitative diagram of these results both when allogenic and xenogeneic transplants were performed.

Moreover, it was surprisingly found that the amniotic membrane can be used to treat heart injuries, particularly after cardiac infarction. By the use of amniotic membrane or pieces or fragments thereof it is possible to reduce infarct size and improve behavioral dysfunction.

Surprisingly it was found that amniotic membrane can be used directly without isolation and purification of cells for treating the heart. It was found that pieces or fragments of amniotic membrane that are directly cut from the amniotic membrane and are fixed at the heart, preferably at least close to the injured part, can improve heart functionality. Tests were made with mice after infarct induction.

In the prior art is was known to use cells derived from the amniotic and/or chorionic membranes of placenta for ameliorating function and reducing infarct size after infarct induction in different animal models. However, the inventor found that the amniotic membrane can be directly used.

It is favourable to use the membrane directly, that is cut in proper pieces or fragment or entirely, because the cells are kept fresh and are not damaged by isolation and cultivation. Moreover, the membrane can be easily fixed at the proper place and held in place for example by sutures. The membrane can be used directly after isolation or can be preserved and used when needed.

Methodology for Preparing the Isolated Amniotic Membrane:

The amniotic membrane from human placenta was mechanically peeled from the chorion.

Coronary infarction was induced in rats according to commonly used established protocols. Briefly, the heart was rapidly exposed through a thoracotomy, followed by ligation of the coronary artery.

Insertion of the freshly obtained (or one day preserved in medium) amniotic membrane: after ligation of the artery and re-positioning of the heart in the thoracic cavity, the intact piece of the amniotic membrane was inserted so to be positioned around the heart and fixed using the same cord as that which had been used for coronary ligation.

Results

Figure 11:
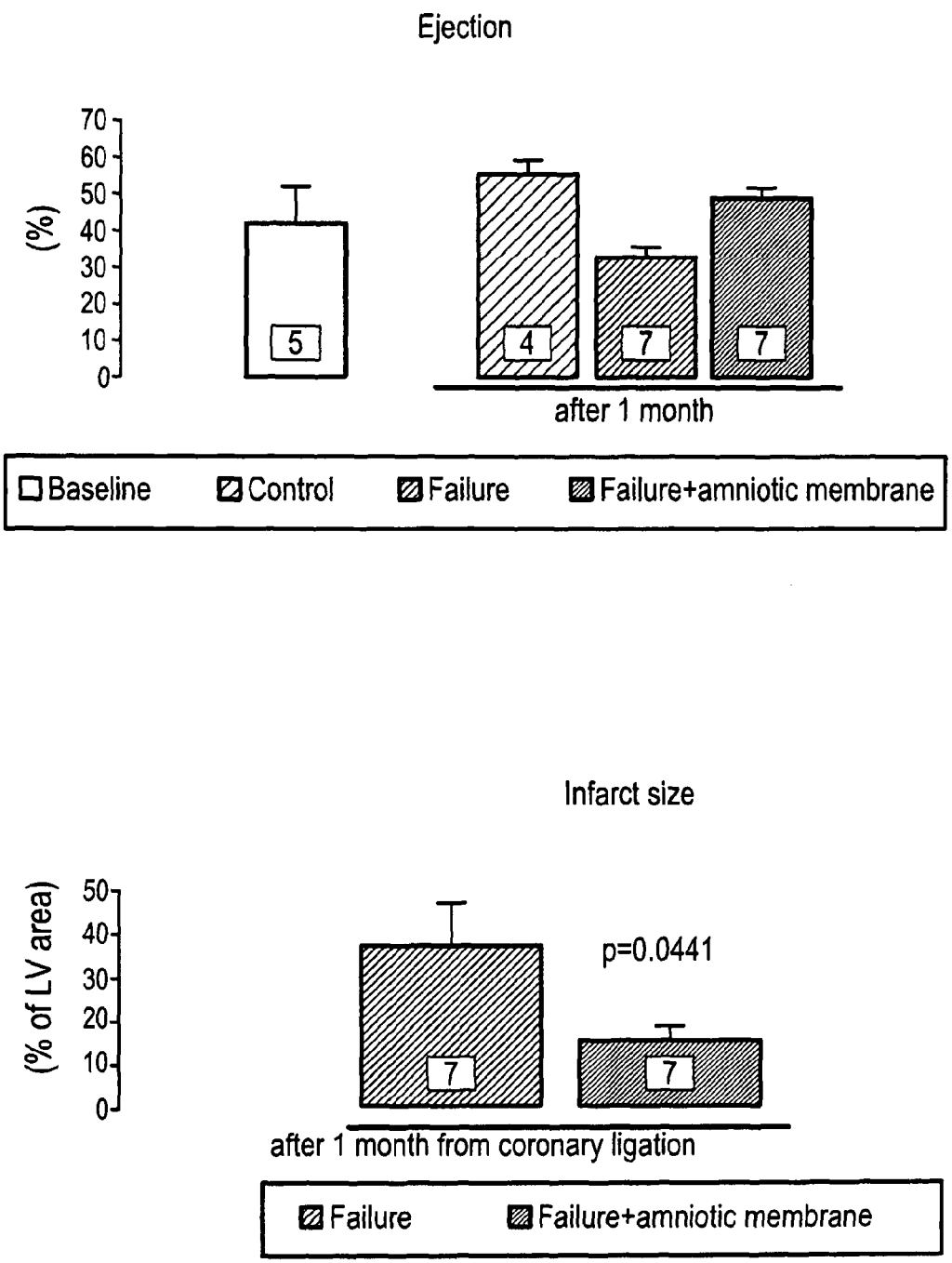
FIG. 11 shows graphs showing an analysis one month after coronary ligation.

Analysis one month after coronary ligation revealed that infarct size was limited in animals which had been treated with amniotic membrane after infarct induction with respect to infarcted, membrane-untreated animals (FIG. 11). Furthermore, improved heart function was also observed in amniotic membrane-treated animals, as demonstrated by a significant increase in the heart ejection fraction in these animals with respect to infracted, untreated animals.

Ejection fraction was calculated as:

$$\frac{LV \text{ End Diastolic } Vol. - LV \text{ End Systolic}}{LD \text{ End Diastolic volume}} vol.$$

The results demonstrate that the amniotic membrane can be directly used for treating the heart, either the whole membrane, or pieces or fragments thereof, without the tedious process of isolating and purifying specific cells. It has been found that the area of infarction can be reduced and the heart function, for example the ejection, can be improved.

FIGURE LEGENDS

FIG. 1. Suppression of allogeneic response by AMTC. Human PBMC (black bars) or human T cells (white bars) were used as responders and incubated with irradiated allogeneic PBMC (PBMC*), either alone or in the presence of AMTC. AMTC were added either in direct contact or in transwell chambers. Proliferation was assessed by [3H]-thymidine incorporation after five days of culture and expressed as a percentage of proliferation observed in the absence of AMTC. Data are mean and SD for more than thirty (PBMC+ PBMC*), or seven independent experiments (T cells+ PBMC*). ***P<0.001 vs. corresponding control sample (Student's t test).

FIG. 2. AMTC inhibitory conditions in MLR. (A) In MLR, responder PBMC were incubated with irradiated allogeneic stimulator PBMC. Increasing concentrations of AMTC were added either in direct contact (□) or in transwell chambers (●). Data are mean±SD from three independent experiments. (B) MLR were performed alone (black bar) or in the presence of supernatants (SN) from AMTC cultures (white bars). SN were collected from days 1 to 6 of AMTC culture. Data are mean and SD from nine independent experiments. *P<0.05, ***P<0.001 vs. corresponding control sample (Student's t test). (C) MLR were performed alone (black bar) or in the presence of AMTC at passage 1 (white bar), passage 2 (gray bar), or passage 3 (hatched bar). AMTC were added either in direct contact or in transwell chambers. Data are mean and SD from three independent experiments. *P<0.05, ***P<0.001 vs. corresponding control sample (Student's t test). (D) MLRs were set up between responder PBMC (R) and equal numbers of allogeneic stimulator PBMC (S1*), with and without the addition of an equal number of AMTC in a transwell chamber. Responders which had been inhibited by AMTC (Ri) were then collected and re-stimulated with the original (Ri+S1*) or third party (Ri+2*) irradiated allogeneic PBMC, in the absence of AMTC. Data are mean and SD from three independent experiments. *P<0.001 vs. corresponding control sample (Student's t test). FIG. 3. Effect of AMTC on unstimulated and CD3, CD3/CD28 stimulated PBMC and T cells. PBMC and T cells were either cultured alone (A), or stimulated with anti-CD3 plus anti-CD28 antibody (B), or with anti-CD3 antibody alone (C). All experiments were performed in the absence (black bars) or presence (white bars) of AMTC, both in direct cell contact and in transwell systems. Proliferation was assessed by [3H]-thymidine incorporation after culturing and expressed in counts per minute (cpm). Data are mean and SD from at least three independent experiments. P<0.01, ***P<0.001 vs. corresponding control sample (Student's t test). FIG. 4. Representative FACS analysis of cells isolated from the mesenchymal amniotic region. (A) Gating strategies to characterize AMTC. R1 was defined based on Side (SSC) and Forward (FSC) Scatter properties of AMTC. (i). Analysis of R1 events using FLH-3 shows two distinct subpopulations, individuated by gates R2 and R3 (ii) that can be back-gated to R1 (iii). (B) Surface expression of HLA-DR in total (gate R1) and R2- and R3-gated AMTC. (C) Surface expression of indicated hematopoietic markers on cells gated in R2 (HLA-DR-positive cells). Red histograms show positive cells, while black histograms show IgG isotype control stainings. Percentages of positive cells are indicated. FIG. 5. Determination of subpopulations present in the mesenchymal amniotic region. (A) Immunohistochemical staining of representative paraffin sections of term placental amniotic and chorionic membranes. CTC (chorionic trophoblastic cells), CMC (chorionic mesenchymal cells), AEC (amniotic epithelial cells), AMTC (amniotic mesenchymal cells). Left panel: section stained with anti-human CD68 antibody; middle panel: section stained with anti-human HLA-DR antibody; right panel: section stained with anti-human CD45RO antibody. Original magnification ×40. (B) RFLP analysis of DNA extracted from HLA-DR+AMTC. Placental deciduas and total AMTC were used as maternal and fetal controls, respectively.

FIG. 6. Effect of cells isolated from mesenchymal amniotic region on CD3 stimulated T cells. (A) Purified T cells were cultured alone or in direct contact with unfractionated, HLA-DR-negative or HLA-DR-positive AMTC, with or without anti-CD3. T cells proliferation was assessed by [3H]-thymidine incorporation after three days of culture and expressed in counts per minute (cpm). Data are mean and SD from at least four independent experiments. ***P<0.001 vs. corresponding control sample (Student's t test). (B) Purified T cells, stimulated with anti-CD3, were cultured alone or in direct contact with increasing concentrations of total AMTC (●), HLA-DR-negative (■) or HLA-DR-positive (▲) AMTC. T cells proliferation was measured by [3H]-thymidine incorporation after two-three days of culture and expressed in counts per minute (cpm). Data are mean and SD from three independent experiments. (C) Purified T cells, stimulated with anti-CD3, were cultured alone or in direct contact with total AMTC cultured for different numbers of passages. At each AMTC passage, the percentage of HLA-DR-positive cells present measured by FACS analysis is reported. T cells proliferation was assessed by [3H]-thymidine incorporation after three days of culture and expressed in counts per minute (cpm). Representative results of three independent experiments are shown.

FIG. 7. Effect of amnion mesenchymal cells on purified T cells stimulated by CD3 plus CD28. (A) Purified T cells, stimulated with anti-CD3 and anti-CD28, were cultured alone or in presence of increasing concentrations of total AMTC, in either direct contact (●) or in transwell chambers (▲). T cells proliferation was assessed by [3H]-thymidine incorporation after two-three days of culture and expressed in counts per minute (cpm). Data are mean and SD from three independent experiments. (B) Purified T cells, stimulated with anti-CD3 and anti-CD28, were cultured alone or in direct contact with increasing concentrations of total AMTC (●), HLA-DR-negative (■) or HLA-DR-positive (▲) AMTC. T cells proliferation was measured by [3H]-thymidine incorporation after two-three days of culture and expressed in counts per minute (cpm). Data are mean and SD from three independent experiments.

Figure 8A:
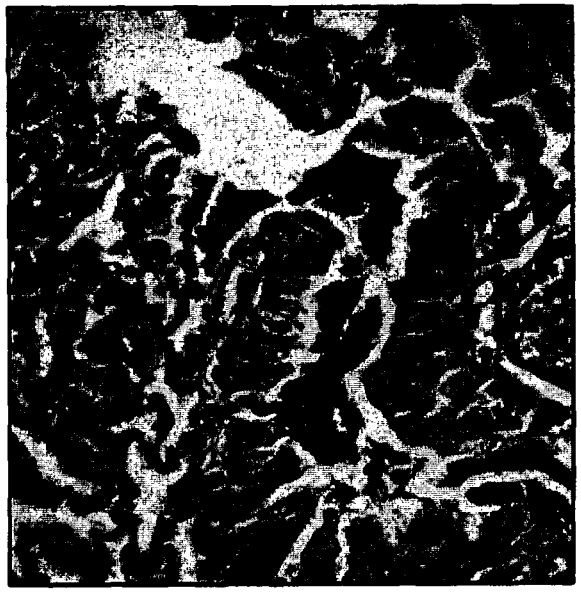
FIG. 8A shows the results of immunohistochemical analyses of a lung microchimerism 3 days from transplantation.
Figure 8B:
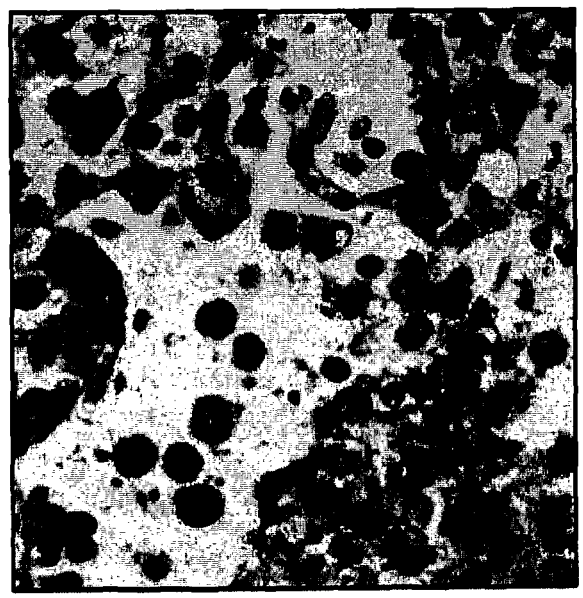
FIG. 8B shows the results of immunohistochemical analyses of a lung microchimerism 14 days from transplantation.

FIG. 8 shows immunohistochemical analyses of lung microchimerism, particularly the microchimerism after intra-tracheal (A) and intra-peritoneal (B) xenotransplantation. Diagram (A) shows the results after 3 days from transplantation and diagram (B) shows the results after 14 days from transplantation FIG. 9 demonstrates that transplantation of placenta-derived cells decreases the lung fibrosis induced by bleomycin. Masson's staining shows a clear reduction of collagen deposition (day 14) in lung treated with cells from fetal membranes (bleo+cells), versus animals treated only with bleomycin (bleo)

FIG. 10 demonstrates the reduction of fibrosis (expressed as score values) in allogenic and xenogenic transplantation (bleo+cell) versus animals only treated with bleomycin (bleo group) and FIG. 11 provides the analysis one month after coronary ligation revealed that infarct size was limited in animals which had been treated with amniotic membrane after infarct induction with respect to infarcted, membrane-untreated animals (FIG. 7). Furthermore, the heart ejection fraction in these animals with respect to infracted, untreated animals is shown.

The invention claimed is:

1. A method of treating lung fibrosis in a subject, which comprises: administering to the subject a medicament including amniotic mesenchymal tissue cells (AMTC) and/or chorionic mesenchymal tissue cells (CMTC), and/or the supernatant from at least 4 day AMTC and/or CMTC culture, and/or AMTC and/or CMTC that is depleted of HLA-DR-positive cells.

2. The method of claim 1, wherein the AMTC and/or CMTC are obtained with a method comprising:
   a) isolating amniotic membrane and/or chorionic membrane from human placenta and/or separating amniotic and chorionic membrane;
   b) washing the membrane of step a) to remove contaminants;
   c) cutting the membrane of step b) into membrane fragments;
   d) incubating the membrane fragments in a medium containing dispase for about 5 minutes to about 15 minutes at about 33° C. to about 42° C.;
   e) incubating the membrane fragments in a resting solution for about 5 minutes to about 15 minute at room temperature;
   f) repeating steps d) and e) 0 to 6 times;
   g) if chorionic membrane is involved, peeling the stromal layer from the trophoblastic layer of the chorionic membrane of step e) or f);
   h) digesting the membrane fragments with collagenase for about 1 hour to about 5 hours at about 33° C. to about 42° C.; and
   i) collecting one or more AMTC and/or CMTC from a suspension obtained in step h).

3. The method of claim 1, wherein the AMTC and/or CMTC are obtained with a method comprising separating fresh preparations of AMTC and/or CMTC, optionally by using immobilized anti-HLA-DR antibody, and eluting HLA-DR-positive cells and/or HLA-DR-negative cells.

4. The method of claim 3, wherein separating includes first incubating AMTC and/or CMTC with anti-HLA-DR antibody coated on magnetic beads and then isolating HLA-DR-positive and/or HLA-DR-negative fractions using magnetic columns.

5. The method of claim 1, wherein the medicament is a cell therapy preparation.

6. The method of claim 1, wherein the medicament includes HLA-DR-negative cells from AMTC and/or CMTC to suppress a T-cell response.

7. The method of claim 1, wherein the medicament includes HLA-DR-positive cells from AMTC and/or CMTC to stimulate lymphocyte proliferation.

8. The method of claim 1, wherein the medicament includes a supernatant obtained from at least 4 day AMTC and/or CMTC culture.

9. The method of claim 8, wherein AMTC and/or CMTC are cultured at a density of $1 \times 10^6$ cells/well in a final volume of 1 mL of RPMI complete medium, and wherein the supernatant is collected after at least 4 days of culture, centrifuged, and filtered.

10. The method of claim 8, wherein the supernatant is obtained from at least 4 day culture of one or more fragments of amniotic membrane and/or chorionic membrane.

11. The method of claim 1, wherein the medicament is administered by an intrapulmonary route.

12. The method of claim 1, wherein the medicament is administered by an intrabronchial route.

13. The method of claim 1, wherein the medicament is administered by an intratracheal route.

14. The method of claim 1, wherein the medicament is administered by an intrajugular route.

15. The method of claim 1, wherein the medicament is administered by an intraperitoneal route.

* * * * *